(12) United States Patent
Christianson et al.

(10) Patent No.: US 7,441,360 B2
(45) Date of Patent: Oct. 28, 2008

(54) AIR FRESHENER WITH PICTURE FRAME

(75) Inventors: Jeffrey J. Christianson, Oak Creek, WI (US); Simon M. Conway, Burlington, WI (US); Stacey L. Forkner, Waterford, WI (US); Kristopher W. Gerulski, Racine, WI (US); Kara L. Lakatos, Racine, WI (US); Stephen B. Leonard, Franksville, WI (US); Heather R. Schramm, Whitewater, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 140 days.

(21) Appl. No.: 11/395,357

(22) Filed: Mar. 31, 2006

(65) Prior Publication Data

US 2006/0196965 A1     Sep. 7, 2006

Related U.S. Application Data

(63) Continuation-in-part of application No. 10/881,816, filed on Jun. 30, 2004, now Pat. No. 7,213,770, which is a continuation-in-part of application No. 11/337,277, filed on Jan. 23, 2006, which is a continuation-in-part of application No. 11/118,500, filed on Apr. 29, 2005.

(51) Int. Cl.
*A47G 1/06* (2006.01)
(52) U.S. Cl. .................................. 40/725; 362/276
(58) Field of Classification Search ................ 40/406, 40/407; 362/276; 239/60, 57, 55
See application file for complete search history.

(56) References Cited

U.S. PATENT DOCUMENTS

| | | | |
|---|---|---|---|
| 882,710 A | 3/1908 | Pearsall | |
| 886,840 A | 5/1908 | Mueller | |
| 1,068,621 A | 7/1913 | Abraham | |
| 1,204,934 A | 11/1916 | Burford et al. | |
| 1,261,133 A | 4/1918 | Kidd | |
| 1,802,999 A | 4/1931 | Budd | |
| 1,815,841 A * | 7/1931 | Gastgivar | 40/766 |
| 1,940,328 A | 12/1933 | Schrotenboer | |
| 2,268,529 A | 12/1941 | Stiles | |

(Continued)

FOREIGN PATENT DOCUMENTS

EP     0 645 081     7/2001

(Continued)

OTHER PUBLICATIONS

International Search Report and Written Opinion dated Aug. 2, 2007 for PCT/US2007/008035.

(Continued)

*Primary Examiner*—Joanne Silbermann
*Assistant Examiner*—Shin Kim

(57) ABSTRACT

A picture display frame includes front and rear sides. A recess is disposed within the rear side of the display frame. A volatile material holder is disposed within the recess of the rear side. The volatile material holder includes a reservoir and a vapor permeable membrane. A slot is disposed in a side wall of the display frame in communication with a portion of the recess. The portion of the recess is adapted to hold a decorative element.

20 Claims, 19 Drawing Sheets

U.S. PATENT DOCUMENTS

| | | | |
|---|---|---|---|
| 2,469,656 A | 5/1949 | Lienert | |
| 2,550,954 A | 5/1951 | Benedict | |
| 2,577,320 A | 12/1951 | Fenyo | |
| 2,579,715 A | 12/1951 | Wilson et al. | |
| D169,871 S | 6/1953 | Speer et al. | |
| 2,779,624 A | 1/1957 | Friedman | |
| 2,840,689 A | 6/1958 | Kazor | |
| 3,178,844 A | 4/1965 | Christian | |
| 3,424,380 A * | 1/1969 | Curran | 239/60 |
| 3,540,146 A | 11/1970 | Watkins | |
| 3,558,055 A | 1/1971 | Storchheim | |
| 3,570,160 A | 3/1971 | Spertus | |
| 3,741,711 A | 6/1973 | Bryant | |
| 3,790,081 A | 2/1974 | Thornton | |
| 3,804,330 A | 4/1974 | Miller, Jr. et al. | |
| 3,822,495 A | 7/1974 | Ohfuji | |
| 3,948,445 A | 4/1976 | Andeweg | |
| D243,402 S | 2/1977 | Irving | |
| 4,009,384 A | 2/1977 | Holland | |
| D247,573 S | 3/1978 | Schimanski | |
| 4,101,720 A | 7/1978 | Taylor et al. | |
| 4,157,787 A | 6/1979 | Schwartz | |
| 4,158,440 A | 6/1979 | Sullivan et al. | |
| 4,161,283 A | 7/1979 | Hyman | |
| 4,165,573 A | 8/1979 | Richards | |
| 4,170,080 A | 10/1979 | Bergh et al. | |
| 4,173,604 A | 11/1979 | Dimacopoulos | |
| 4,184,099 A | 1/1980 | Lindauer et al. | |
| 4,285,468 A | 8/1981 | Hyman | |
| D260,503 S | 9/1981 | Stangarone | |
| 4,293,095 A | 10/1981 | Hamilton et al. | |
| 4,314,915 A | 2/1982 | Weigers | |
| D263,334 S | 3/1982 | Schimanski | |
| 4,327,056 A | 4/1982 | Gaiser | |
| D269,838 S | 7/1983 | Altonga | |
| 4,411,829 A | 10/1983 | Schulte-Elte | |
| D271,359 S | 11/1983 | Le | |
| 4,434,306 A | 2/1984 | Kobayashi | |
| D275,223 S | 8/1984 | Marxen | |
| D275,700 S | 9/1984 | Marxen | |
| 4,476,171 A | 10/1984 | Takeuchi | |
| 4,493,011 A | 1/1985 | Spector | |
| D279,146 S | 6/1985 | McCaffrey | |
| D280,363 S | 9/1985 | Wisecup, Jr. | |
| 4,549,250 A | 10/1985 | Spector | |
| 4,580,581 A | 4/1986 | Reece et al. | |
| D288,003 S | 1/1987 | Hoyt | |
| 4,634,614 A | 1/1987 | Holzer | |
| 4,695,435 A | 9/1987 | Spector | |
| 4,714,984 A | 12/1987 | Spector | |
| 4,720,409 A | 1/1988 | Spector | |
| D296,957 S | 8/1988 | Gordon et al. | |
| 4,762,275 A | 8/1988 | Herbert et al. | |
| 4,781,895 A | 11/1988 | Spector | |
| 4,794,714 A | 1/1989 | Weisgerber | |
| 4,809,912 A | 3/1989 | Santini | |
| 4,814,212 A | 3/1989 | Spector | |
| 4,849,606 A | 7/1989 | Martens, III et al. | |
| 4,874,129 A | 10/1989 | DiSapio et al. | |
| 4,883,692 A | 11/1989 | Spector | |
| D305,703 S | 1/1990 | Wang | |
| 4,898,328 A | 2/1990 | Fox et al. | |
| 4,913,349 A | 4/1990 | Locko | |
| 4,917,301 A | 4/1990 | Munteanu | |
| 4,921,636 A | 5/1990 | Traas | |
| 4,939,858 A | 7/1990 | Dailey | |
| 4,959,087 A | 9/1990 | Kappernaros | |
| 4,993,177 A | 2/1991 | Hudson | |
| 4,995,555 A | 2/1991 | Woodruff | |
| D320,266 S | 9/1991 | Kunze | |
| 5,060,858 A | 10/1991 | Santini | |
| D325,077 S | 3/1992 | Kearnes | |
| 5,148,983 A | 9/1992 | Muniz | |
| 5,148,984 A | 9/1992 | Bryson et al. | |
| 5,163,616 A | 11/1992 | Bernarducci et al. | |
| 5,170,886 A | 12/1992 | Holzner | |
| 5,219,121 A | 6/1993 | Fox et al. | |
| 5,230,867 A | 7/1993 | Kunze et al. | |
| D339,238 S | 9/1993 | Hamilton | |
| D339,242 S | 9/1993 | Sontag et al. | |
| 5,247,745 A | 9/1993 | Valentino | |
| 5,259,555 A | 11/1993 | Kiefer | |
| 5,297,732 A | 3/1994 | Hahn | |
| D346,068 S | 4/1994 | White | |
| 5,304,358 A | 4/1994 | Hoyt et al. | |
| 5,334,361 A | 8/1994 | Rafaelides et al. | |
| 5,361,522 A * | 11/1994 | Green | 40/725 |
| 5,367,802 A | 11/1994 | Rosenberg | |
| D354,627 S | 1/1995 | Rowan | |
| 5,395,047 A | 3/1995 | Pendergrass, Jr. | |
| 5,402,517 A | 3/1995 | Gillett et al. | |
| D358,037 S | 5/1995 | Monroe | |
| D360,461 S | 7/1995 | Gillespie | |
| 5,439,100 A | 8/1995 | Gordon et al. | |
| D361,896 S | 9/1995 | Bramley et al. | |
| 5,462,006 A | 10/1995 | Thiruppathi | |
| D366,107 S * | 1/1996 | Shaffer | D23/366 |
| 5,503,332 A | 4/1996 | Glenn | |
| D369,473 S | 5/1996 | Gluck | |
| 5,529,243 A | 6/1996 | Hoyt et al. | |
| D372,797 S | 8/1996 | Ilaria et al. | |
| 5,556,192 A * | 9/1996 | Wang | 362/276 |
| D374,777 S | 10/1996 | Agam | |
| D376,002 S | 11/1996 | Upson | |
| D376,420 S | 12/1996 | Rymer | |
| D376,914 S | 12/1996 | Waszkiewicz | |
| D380,822 S | 7/1997 | Decker et al. | |
| 5,647,052 A | 7/1997 | Patel et al. | |
| 5,651,942 A | 7/1997 | Christensen | |
| D383,613 S | 9/1997 | Handler | |
| D384,821 S | 10/1997 | Sugar | |
| 5,679,334 A | 10/1997 | Semoff et al. | |
| 5,711,955 A | 1/1998 | Karg | |
| 5,716,000 A | 2/1998 | Fox | |
| D392,031 S | 3/1998 | Miller | |
| D392,032 S | 3/1998 | Zaragoza et al. | |
| 5,735,460 A | 4/1998 | Eisenbraun | |
| 5,744,106 A | 4/1998 | Eagle | |
| 5,749,519 A | 5/1998 | Miller | |
| 5,749,520 A | 5/1998 | Martin et al. | |
| 5,782,409 A | 7/1998 | Paul | |
| 5,788,155 A | 8/1998 | Martin et al. | |
| 5,804,264 A | 9/1998 | Bowen | |
| D399,298 S | 10/1998 | Whitehead | |
| D401,767 S | 12/1998 | Leung | |
| 5,845,847 A | 12/1998 | Martin et al. | |
| D405,473 S | 2/1999 | Tikhonski et al. | |
| D405,961 S | 2/1999 | Stangl | |
| 5,875,968 A | 3/1999 | Miller et al. | |
| 5,885,701 A | 3/1999 | Berman et al. | |
| D407,809 S | 4/1999 | Hammond | |
| 5,899,382 A | 5/1999 | Hayes et al. | |
| 5,950,922 A * | 9/1999 | Flinn | 239/34 |
| 5,961,043 A | 10/1999 | Samuelson | |
| 5,975,427 A | 11/1999 | Harries | |
| 6,031,967 A * | 2/2000 | Flashinski et al. | 392/390 |
| D424,812 S | 5/2000 | Kacius | |
| 6,065,687 A | 5/2000 | Suzuki et al. | |
| 6,106,786 A | 8/2000 | Akahoshi | |
| 6,109,537 A | 8/2000 | Heath | |
| D431,075 S | 9/2000 | Barraclough | |
| 6,112,496 A | 9/2000 | Hugus et al. | |
| 6,144,801 A | 11/2000 | Lehoux et al. | |
| 6,152,379 A | 11/2000 | Sorgenfrey | |

| | | | |
|---|---|---|---|
| 6,154,607 A | 11/2000 | Flashinski et al. | |
| D435,100 S | 12/2000 | Pesu et al. | |
| D437,404 S | 2/2001 | Wu | |
| 6,203,394 B1 * | 3/2001 | Lee | 446/159 |
| D439,964 S | 4/2001 | Wu | |
| D441,441 S | 5/2001 | Upson | |
| D445,262 S | 7/2001 | Rowan | |
| 6,254,248 B1 | 7/2001 | McAuley et al. | |
| 6,254,836 B1 | 7/2001 | Fry | |
| D451,990 S | 12/2001 | Millet | |
| 6,328,935 B1 | 12/2001 | Buccellato | |
| D453,561 S | 2/2002 | Nelson | |
| 6,354,710 B1 | 3/2002 | Nacouzi | |
| 6,358,577 B1 | 3/2002 | Bowen et al. | |
| 6,363,734 B1 | 4/2002 | Aoyagi | |
| 6,367,706 B1 | 4/2002 | Putz | |
| D456,620 S | 5/2002 | Vincent | |
| D456,888 S | 5/2002 | Buthier | |
| D461,006 S | 7/2002 | Buthier | |
| D461,393 S | 8/2002 | Aubert | |
| 6,435,423 B2 | 8/2002 | Hurry et al. | |
| 6,478,440 B1 | 11/2002 | Jaworski et al. | |
| 6,484,425 B1 | 11/2002 | Hirsch | |
| 6,526,636 B2 | 3/2003 | Bernhardt | |
| 6,548,015 B1 | 4/2003 | Stubbs et al. | |
| 6,555,068 B2 | 4/2003 | Smith | |
| D476,726 S | 7/2003 | Rosenberg | |
| 6,610,254 B1 | 8/2003 | Furner et al. | |
| D479,742 S | 9/2003 | Hollingsworth | |
| 6,618,974 B2 * | 9/2003 | Szalay | 40/611.06 |
| 6,627,857 B1 | 9/2003 | Tanner et al. | |
| D480,221 S | 10/2003 | Luciano | |
| D481,113 S | 10/2003 | Groene et al. | |
| 6,631,852 B1 | 10/2003 | O'Leary | |
| 6,638,591 B2 | 10/2003 | Bowen et al. | |
| D481,785 S | 11/2003 | Koike | |
| 6,643,967 B1 | 11/2003 | Bloom | |
| 6,648,239 B1 | 11/2003 | Myny et al. | |
| 6,663,838 B1 | 12/2003 | Soller et al. | |
| D485,607 S | 1/2004 | Wu | |
| D487,308 S | 3/2004 | Engerant | |
| 6,705,541 B2 | 3/2004 | Schuehrer et al. | |
| 6,714,725 B2 | 3/2004 | Grone et al. | |
| 6,722,578 B2 | 4/2004 | Shalitzky et al. | |
| 6,730,311 B2 | 5/2004 | Maleeny et al. | |
| 6,749,672 B2 * | 6/2004 | Lynn | 96/222 |
| 6,790,436 B2 | 9/2004 | Williams et al. | |
| 6,808,791 B2 | 10/2004 | Curro et al. | |
| D498,524 S | 11/2004 | Morillas | |
| D498,525 S | 11/2004 | Harbutt et al. | |
| D498,836 S | 11/2004 | Morillas | |
| 6,826,863 B1 * | 12/2004 | Goodfellow | 40/725 |
| 6,998,581 B2 | 2/2006 | Currie | |
| 7,028,917 B2 | 4/2006 | Buthier | |
| 7,036,747 B2 | 5/2006 | Channer | |
| 7,138,367 B2 | 11/2006 | Hurry et al. | |
| 7,175,815 B2 | 2/2007 | Yamasaki et al. | |
| 2003/0007887 A1 | 1/2003 | Roumpos et al. | |
| 2003/0085297 A1 | 5/2003 | Huang | |
| 2003/0089791 A1 | 5/2003 | Chen et al. | |
| 2003/0094503 A1 | 5/2003 | Rymer et al. | |
| 2003/0200690 A1 | 10/2003 | Galloway | |
| 2004/0000596 A1 | 1/2004 | Cuthbert | |
| 2004/0057975 A1 | 3/2004 | Maleeny et al. | |
| 2004/0262418 A1 | 12/2004 | Smith et al. | |
| 2005/0001337 A1 | 1/2005 | Pankhurst | |
| 2005/0103880 A1 | 5/2005 | Taite | |
| 2005/0145711 A1 | 7/2005 | Blondeau et al. | |
| 2005/0196571 A1 | 9/2005 | Penny et al. | |
| 2006/0000920 A1 | 1/2006 | Leonard | |

FOREIGN PATENT DOCUMENTS

| | | |
|---|---|---|
| EP | 1 346 734 | 9/2003 |
| GB | 2 254 558 | 10/1992 |
| GB | D3003643 | 11/2002 |
| GB | D3003644 | 6/2003 |
| GB | D3005517 | 7/2003 |
| GB | D3007046 | 9/2003 |
| GB | D3007049 | 9/2003 |
| GB | D3007052 | 9/2003 |
| GB | D3007053 | 9/2003 |
| GB | D3007054 | 9/2003 |
| GB | D3007055 | 9/2003 |
| GB | D3007056 | 9/2003 |
| GB | D3007057 | 9/2003 |
| GB | D3007233 | 9/2003 |
| GB | D3007045 | 10/2003 |
| GB | D3007048 | 10/2003 |
| GB | D3012024 | 2/2004 |
| GB | D3012025 | 2/2004 |
| GB | D3012026 | 2/2004 |
| JP | HA05015803 | 8/1993 |
| JP | 08-241039 | 9/1996 |
| JP | 09084863 A | 3/1997 |
| JP | D1027932 | 9/1998 |
| JP | 10263068 A | 10/1998 |
| JP | D1195937 | 2/2004 |
| NL | 000205661-0001 | 10/2004 |
| NL | 000252358-0001 | 2/2005 |
| NL | 000252366-0001 | 2/2005 |
| WO | WO 96/33605 | 10/1996 |
| WO | WO 00/23121 | 4/2000 |
| WO | WO 03/068276 | 8/2003 |
| WO | WO 2007/096432 | 8/2007 |

OTHER PUBLICATIONS http://www.glade.com/piso.asp.
http://www.glade.com/plugins.asp.
http://www.airwick.us/product_page/product.html.
http://www.racerwheel.com/tcr-cz-103.html.
http://www.racerwheel.com/tcr-cz-102a.html.
http://www.giftsandgadgetsonline.com/ioairfrwilif.html.
http://www.allproducts.com/gift/sundeal/02-ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ-201ionicfreshener.html.
http://www.buylighting.com/Odor_eliminating_light_bulbs.html.
International Search Report and Written Opinion dated Sep. 12, 2005, Appl. No. PCT/US2005/023226.

* cited by examiner

AIR FRESHENER WITH PICTURE FRAME

CROSS REFERENCE TO RELATED APPLICATIONS

This application is a continuation-in-part of U.S. patent application Ser. No. 10/881,816 now U.S. Pat. No. 7,213,770, which was filed on Jun. 30, 2004, U.S. patent application Ser. No. 11/118,500, which was filed on Apr. 29, 2005, and U.S. patent application Ser. No. 11/337,277, which was filed on Jan. 23, 2006. This application claims the benefit to all such previous applications, and such applications are hereby incorporated herein by reference in their entireties.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a volatile material dispenser, and more particularly, to a volatile material dispenser in combination with a picture frame.

2. Description of the Background

Volatile material dispensers have been used to provide fragrances to office or home settings. One such dispenser is an ornamental design for a combination picture frame and air freshener receptacle. The picture frame is rectangular and has a bottom wall, a top wall, and two side walls. One of the side walls has a slot. An opening extends through a front face of the receptacle. A rear face of the picture frame is provided with an apertured receptacle. The receptacle has side portions that extend outwardly from the rear face of the picture frame and inwardly toward each other. The side portions are inwardly spaced from the side walls and are connected by a planar rear portion.

Another dispenser is an air freshener support for a car with a rectangular housing having a front panel with a rectangular opening disposed therein. A photograph is nested adjacent the opening so that peripheral edges of the photograph are adjacent inner portions of the front panel. A back cover is disposed behind the photograph so as to press and retain same between the front panel and the back cover. A rectangular pad impregnated with a fragrance is disposed adjacent the back cover.

Yet another dispenser is an air freshener picture frame with a rectangular housing having front and rear faces, wherein the front face has a front panel with a rectangular front opening therein, and the rear face has a rear opening. A back panel is disposed within the rear face and presses against a clear sheet and artwork to keep both in place within the rear face. An air freshener material is provided within an enclosure attached to a back side of the back panel, wherein the enclosure has vents to allow diffusion of a fragrance from the material.

SUMMARY OF THE INVENTION

According to one embodiment of the present invention, a picture display frame comprises a display frame having front and rear sides. A recess is disposed within the rear side of the display frame. A volatile material holder is disposed within the recess of the rear side. The volatile material holder includes a reservoir and a vapor permeable membrane. A slot is disposed in a side wall of the display frame in communication with a portion of the recess. The portion of the recess is adapted to hold a decorative element.

According to another embodiment of the present invention, a display frame comprises a frame having front and rear faces. A stepped recess is disposed within the rear face of the frame. The stepped recess includes an outer recess, a medial recess, and an inner recess. A dispenser is disposed within the outer and medial recesses. The dispenser includes a blister and a vapor permeable membrane. A channel is disposed in a side wall of the display frame in communication with the stepped recess. The inner recess is adapted to hold a decorative element.

According to yet another embodiment of the present invention, a frame for displaying a decorative element comprises a frame having a dispenser disposed in a face thereof. A channel extends from an exterior surface of the frame to a void within an interior thereof. The void is defined by a bottom wall of the dispenser directed toward the interior of the frame and recessed portions of the frame. The channel is adapted to allow for the insertion of a decorative element into the void.

BRIEF DESCRIPTION OF THE DRAWINGS

Other aspects and advantages of the present invention will become apparent upon reading the following detailed description and upon reference to the drawings in which.

DETAILED DESCRIPTION OF THE INVENTION

Figure 1:
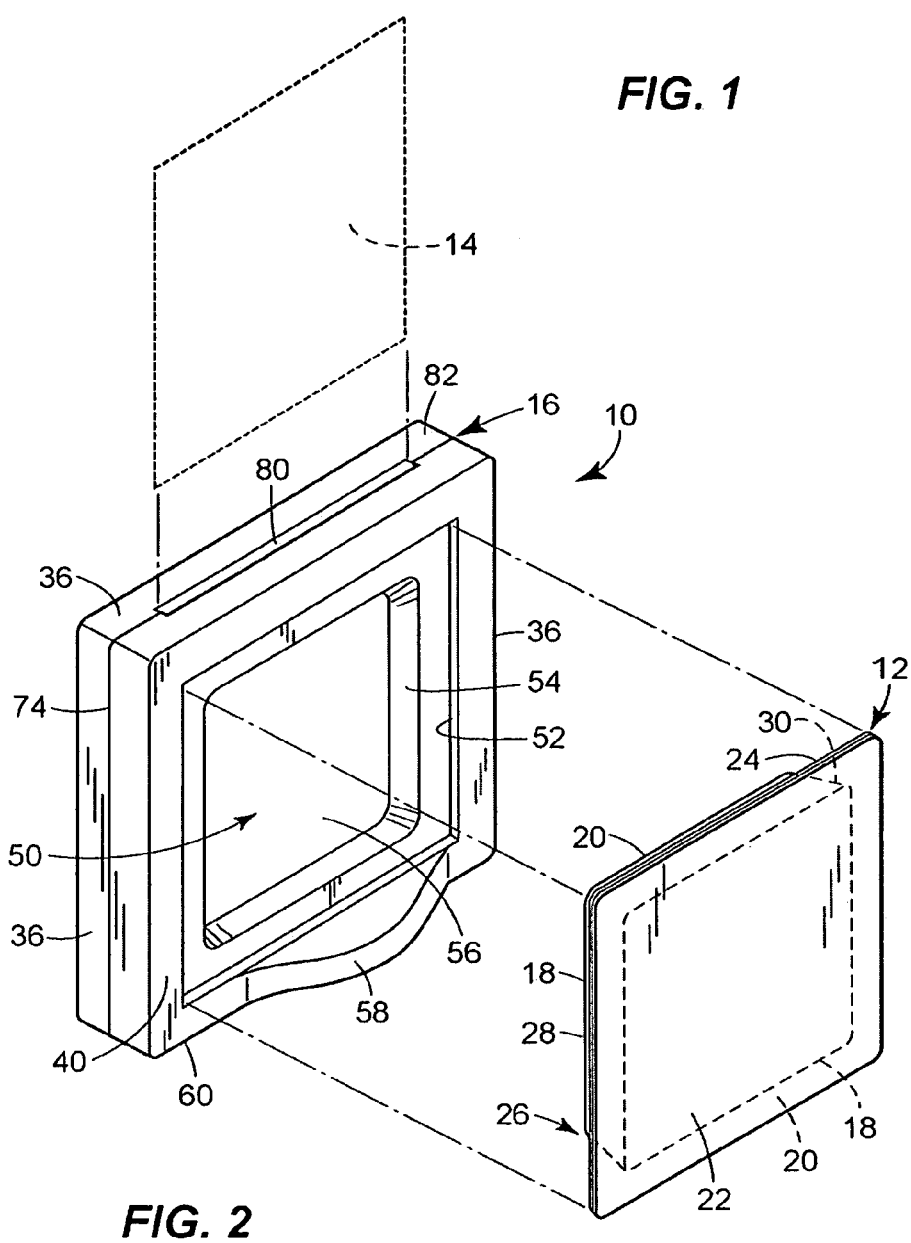
FIG. 1 is an exploded rear isometric view of the volatile material dispensing system that includes a frame, a dispenser, and a decorative element.
Figure 2:
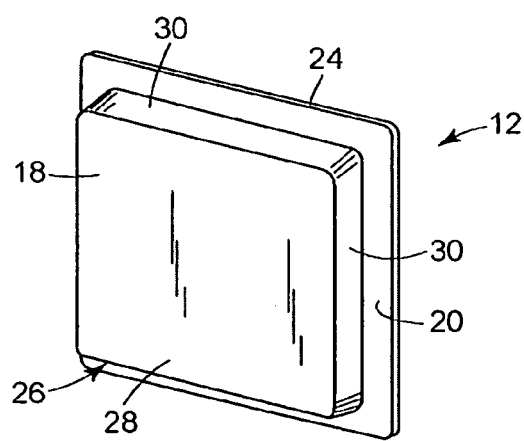
FIG. 2 is an isometric view of the dispenser as shown in FIG. 1.

Referring to FIGS. 1-11, a volatile material dispensing system 10 is illustrated. The dispensing system 10 includes a volatile material dispenser 12, a decorative element 14, and a display frame 16 for holding the dispenser 12 and the decorative element 14. The decorative element 14 may be an image, a photograph, a picture, a drawing, a textile weave, a fabric print, an organic material such as dry leaves, tooled leather, a plastic material, or any other material with aesthetic aspects. Further, the decorative element 14 may be fully or partially functional after insertion into the dispenser 12. For example, the decorative element 14 could provide directions such as how to navigate through a building or the decorative element 14 could be a home shopping list.

With particular reference to FIGS. 1, 2, and 7-9, the dispenser 12 includes a blister 18, a peripheral flange 20, and an impermeable laminate 22 releasably adhered to the blister 18 and the flange 20. The blister 18 includes a non-porous permeable membrane 24 and a cup-shaped structure 26. The cup-shaped structure 26 includes a bottom wall 28 and four side walls 30 that in conjunction with the permeable membrane 24 act as a sealed reservoir to contain a volatile material 32.

Illustratively, the cup-shaped structure 26 is comprised of a recycled polyethylene terephthalate (RPET) layer adhesively bonded to a nylon laminate. The nylon laminate may also include a layer of ethylene vinyl acetate (EVA) coextruded to each side of a middle nylon layer. The nylon laminate and RPET layer of the cup-shaped structure 26 in one embodiment have a thickness of about 0.3 mm (0.012 in.) to about 0.4 mm (0.016 in.). The cup-shaped structure 26 is generally rectangular and/or square with overall dimensions of about 3 mm (0.118 in.) to about 5 mm (0.197 in.) high, about 50 mm (1.969 in.) to about 60 mm (2.362 in.) long, and about 50 mm (1.969 in.) to about 60 mm (2.362 in.) wide. Each cup-shaped structure 26 has four side walls 30. The corresponding side walls 30 each have a height of about 3 mm (0.118 in.) to about 5 mm (0.197 in.) and a width of about 50 mm (1.969 in.) to about 60 mm (2.362 in.). The side walls 30 taper slightly outward as one moves from the bottom wall 28 to the flange 20. The bottom wall 28 is also generally rectangular and has a length of about 48 mm (1.890 in.) to about 58 mm (2.283 in.) and a width of about 48 mm (1.890 in.) to about 58 mm (2.283 in.). The side walls 30 and the bottom wall 28 of the cup-like structure 26 in one embodiment are thermoformed from a single sheet of the RPET and nylon laminate that is heated, then blown and/or pressed into the flange-and-cup arrangement shown in FIG. 2. The cup-shaped structure 26 may be clear and/or translucent, allowing for the visibility of the volatile material 32 contained within the blister 18. In an alternative embodiment, the cup-shaped structure 26 may be colored or otherwise tinted.

The peripheral flange 20 is planar and is coupled to and extends outwardly from top edges of the cup-shaped structure 26. In one embodiment, the peripheral flange 20 extends outwardly from upper edges of the side walls 30. The flange 20 is integrally formed with the cup-shaped structure 26 in, for example, a thermoforming process, as described in the previous paragraph.

Figure 7:
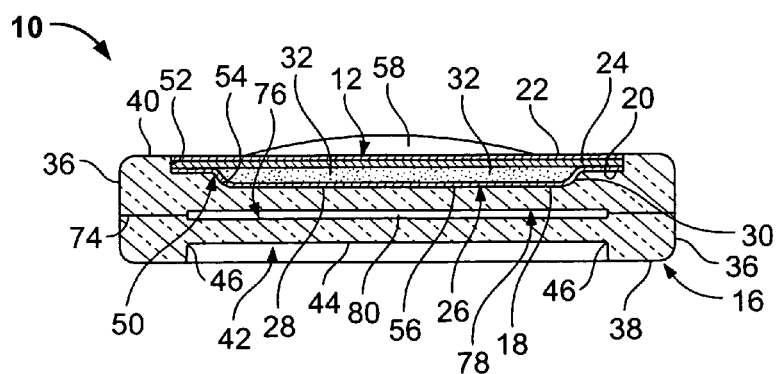
FIG. 7 is a sectional view of the dispensing system taken along the line 7-7 of FIG. 4.
Figure 8:
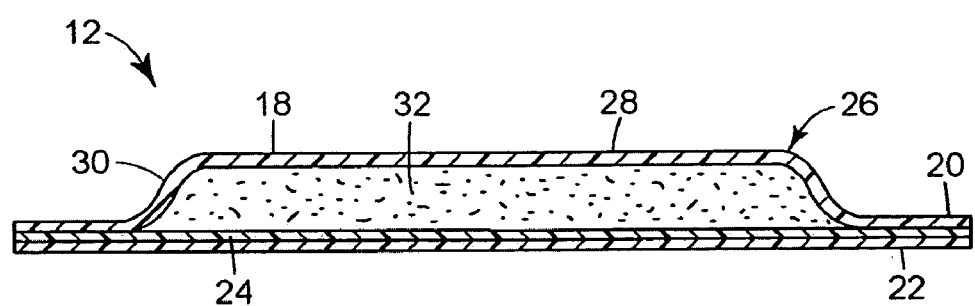
FIG. 8 is a partial enlarged sectional view of the dispenser as shown in FIG. 7 in a filled condition.
Figure 9:
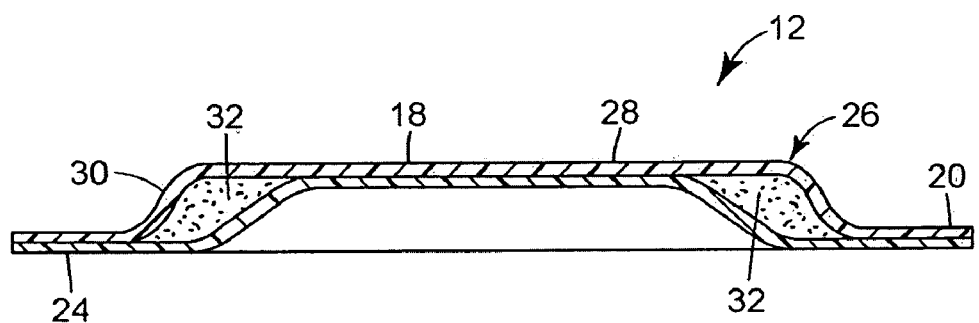
FIG. 9 is a partial enlarged sectional view of the dispenser as shown in FIG. 7 in an unfilled condition.

Illustratively, the permeable membrane 24 has a thickness of about 0.05 mm (0.002 in.) to about 0.15 mm (0.006 in.) The permeable membrane 24 may also be formed integrally with the impermeable laminate 22 and is heat fused to the flange 20 such that the permeable membrane 24 extends across the entire cup-shaped structure 26. FIGS. 7 and 8 show the permeable membrane 24 and the impermeable laminate 22 enclosing and sealing the cup-shaped structure 26 with the volatile material 32 stored inside, thereby forming a thin sealed container impermeable to the volatile material 32 stored inside. This container remains substantially impermeable until the user grasps a corner of the impermeable laminate 22 and peels the impermeable laminate 22 from the permeable membrane 24, thereby exposing the permeable membrane 24 and permitting the volatile material 32 to migrate through the permeable membrane 24 and diffuse into the ambient air (FIG. 9). The permeable membrane 24 is comprised of a co-extrusion of polypropylene (PP) and low density polyethylene (LDPE) and is clear and/or translucent, allowing for visibility of the volatile material 32 contained within the blister 18.

The impermeable laminate 22 may include one or more layers of LDPE, aluminum foil, and/or polyester (PET). In the present embodiment, a layer of LDPE is bonded to one side of an aluminum foil layer and a layer of blended LDPE is adhesively bonded to the other side of the aluminum foil layer. Further, a PET layer is adhesively bonded to the LDPE layer. An extrusion bonding material may be used to bond the layers together. Illustratively, the impermeable laminate 22 has a thickness of between about 0.05 mm (0.002 in.) and about 0.2 mm (0.008 in.). The polyester layer is generally suitable for printing and may be the outer surface of the impermeable laminate 22.

Following placement of the volatile material 32 into the cup-shaped structure 26, a seal is made between the flange 20 and the permeable membrane 24 thereby forming the dispenser 12. As noted above, the impermeable laminate 22 may be attached to the blister 18 at the same time as the permeable membrane 24 if, for example, the impermeable laminate 22 and the permeable membrane 24 are co-extruded. The permeable membrane 24 and impermeable laminate 22 may be attached to the flange 20 of the blister 18 using any conventional means, such as an adhesive, heat sealing, and/or crimping, or the like. The seal is substantially air-tight so as to prevent leakage of air and/or the volatile material 32. The volatile material 32 does not completely fill the void within the blister 18. A relatively small amount of air can be tolerated in the dispenser 12 following the creation of the blister 18. For example, the air in the sealed blister 18 is no more than about 3% to about 10% of the overall volume of the blister 18. As the volatile material 32 diffuses out of the dispenser 12 little or no air enters the blister 18 through the permeable membrane 24. In one embodiment, the permeable membrane 24 is configured to distend and collapse with relatively few or no gas bubbles being formed.

There is substantially no diffusion of the volatile material 32 when the dispenser 12 is filled and the impermeable laminate 22 covers the permeable membrane 24. Illustratively, the impermeable laminate 22 is removed from the blister 18 by a user grasping an end of the impermeable laminate 22 and peeling it off the blister 18. A tab 34, extension, or other means for grasping may be included as an extension of the impermeable laminate 22 to aid in removal of same. The extension may be at the corners, ends, and/or on the surface of the impermeable laminate 22.

Following removal of the impermeable laminate 22, the dispensing system 10 begins to transition from a full or first condition (FIGS. 7 and 8) to an empty or second condition (FIG. 9). There may be a small amount of the volatile material 32 that remains in the blister 18 and the dispenser 12 will still be considered to have reached the second condition. As the volatile material 32 diffuses through the permeable membrane 24, the permeable membrane 24 slowly collapses upon the bottom wall 28. With reference to FIG. 9, following diffusion of the volatile material 32 across the permeable membrane 24 there is less volatile material 32 contained within the dispenser 12. Substantially no new air enters the dispenser 12 subsequent to diffusion of the volatile material 32. The result of this is a pressure gradient across the permeable membrane 24, with a higher pressure existing in the ambient air than the pressure in the dispenser 12. The pressure gradient causes the ambient air to exert a net positive pressure upon the dispenser 12, which presses the permeable membrane 24 against the remaining volatile material 32 and ultimately the bottom wall 28. Continued diffusion of the volatile material 32 increases the force exerted upon the permeable membrane 24, which causes the remaining volatile material 32 to migrate from a center of the bottom wall 28 toward a periphery of the bottom wall 28. Continued migration and diffusion of the volatile material 32 results in an increasing surface area contact between the permeable membrane 24 and the bottom wall 28 until the dispenser 12 is empty, or nearly empty. The pressure gradient ultimately resulting in migration of the volatile material 32 may also be viewed as occurring due to an increasing compressed vacuum presence within the dispenser 12 as the volatile material continues to diffuse across the permeable membrane 24.

A small amount of the volatile material 32 may remain within the dispenser 12 when it is nearly empty. The volatile material 32 will typically be present in the form of a ring-like appearance (not shown) toward the periphery of the bottom wall 28. However, in other embodiments the pressure gradient between the ambient air and the interior of the dispenser 12 is reduced, thereby diminishing the tendency of the remaining volatile material 32 to form a ring-like appearance. In yet other embodiments, the concentration of certain thickening agents imparts a dry crystalline appearance to the remaining volatile material 32. In one embodiment, a dye and thickener combine to comprise approximately 1% to 3% of the overall volatile material 32 composition of the dispensing system 10 at the first condition. In a different embodiment, the dye and thickener combine to comprise approximately 2% of the overall volatile material 32 composition of the dispensing system 10 at the first condition. A higher composition of dye is present in the volatile material 32 when the dispenser 12 is nearly empty, as the dye utilized does not easily diffuse across the permeable membrane 24. The higher accumulation of dye results in a more readily viewable ring-like appearance. The color of the ring-like image is a more intense color than the coloration of the first condition because of the increased concentration of the dye material. In the second condition the thickener and dye comprise nearly all of the material left within the dispenser 12. Of course, this may change dependent upon the particular dye composition and thickening agent utilized in the volatile material 32.

Figure 3:
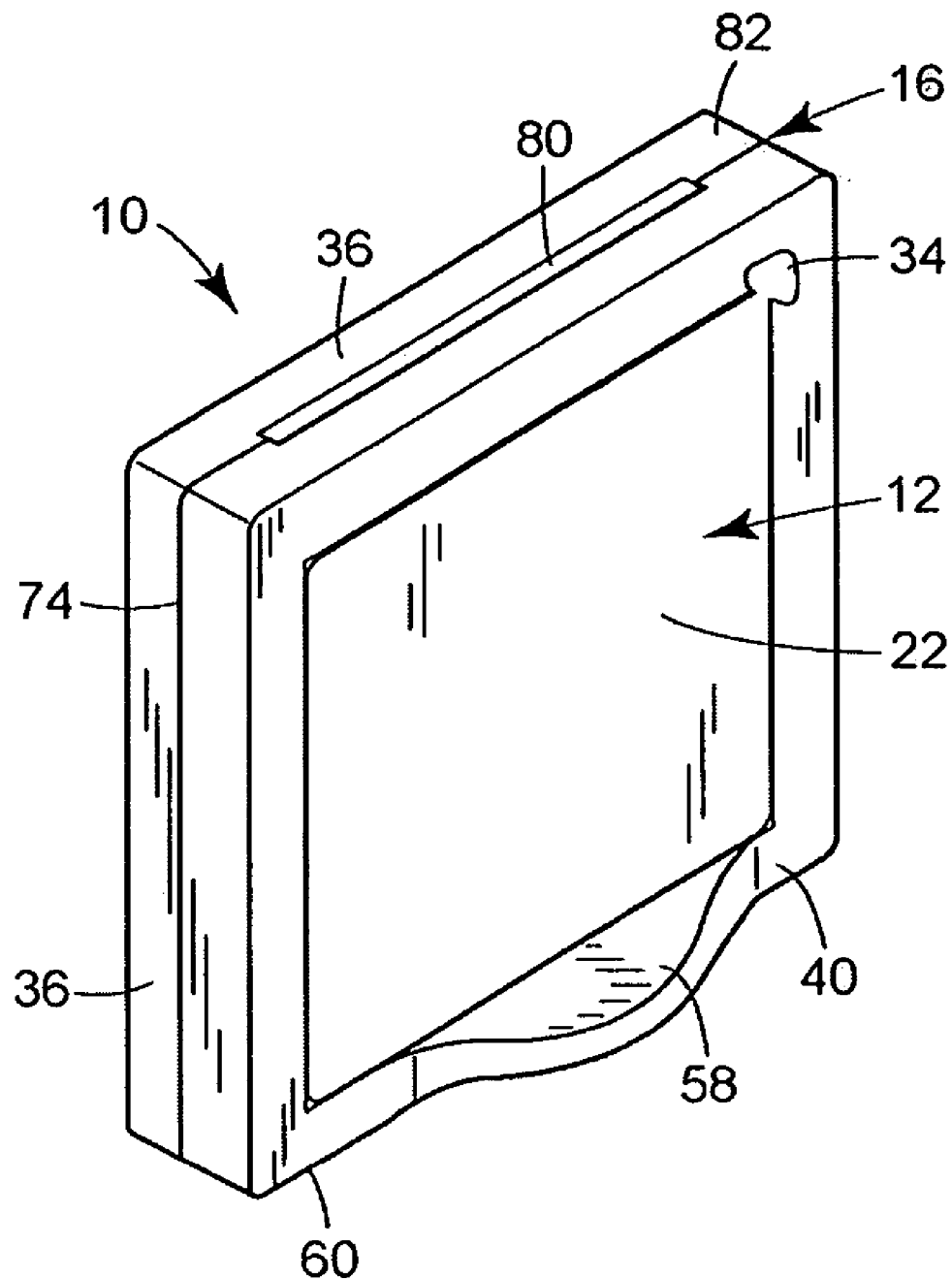
FIG. 3 is a rear isometric view of the assembled dispensing system shown in FIG. 1.
Figure 4:
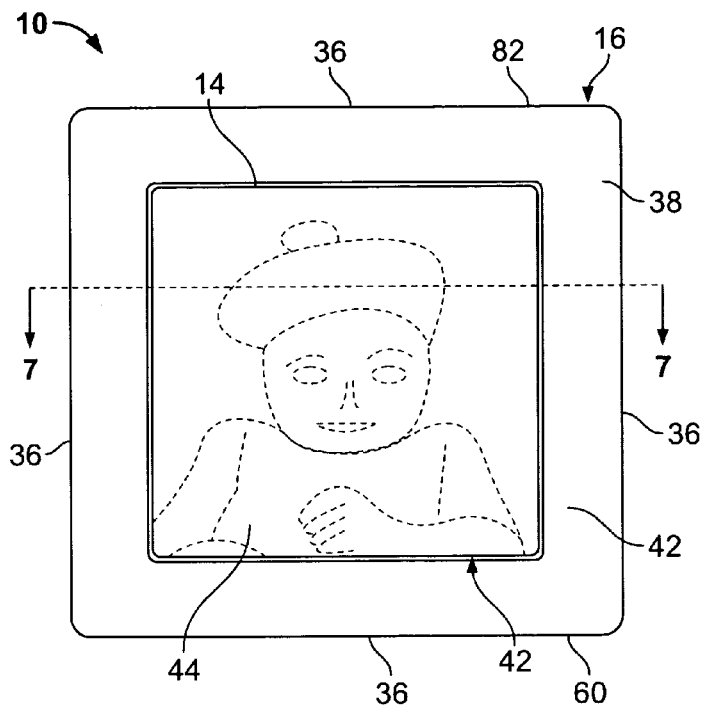
FIG. 4 is a front elevational view of the dispensing system of FIG. 3.
Figure 5:
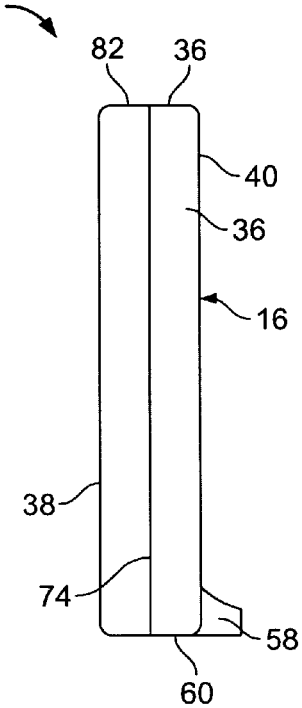
FIG. 5 is a side elevational view of the dispensing system of FIG. 3.
Figure 6:
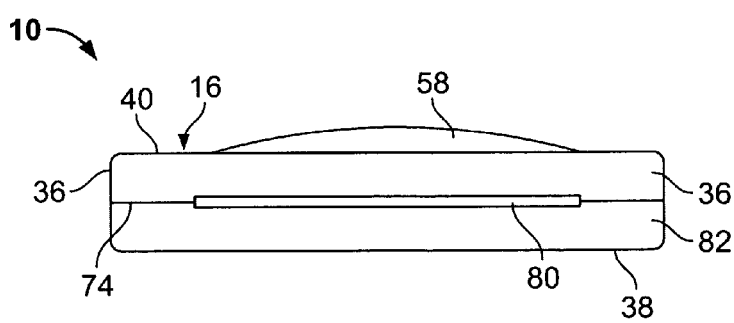
FIG. 6 is a plan view of the dispensing system of FIG. 3.

The display frame 16 is a rectangular structure with four substantially equal-sized side walls 36 (FIGS. 1, 3, 5, and 6), a front face 38 (FIG. 4), and a rear face 40 (FIGS. 1 and 3). In one embodiment, the display frame 16 has a thickness within a range of about 12 mm (0.472 in.) to about 22 mm (0.866 in.) and a height and width within a range of about 70 mm (2.756 in.) to about 90 mm (3.543 in.). In another embodiment, the display frame 16 has a thickness of about 16 mm (0.630 in.) and a height and width of about 86 mm (3.386 in.). The front face 38 of the display frame 16 in one embodiment has a surface area greater than or equal to about 3000 mm$^2$.

The front face 38 of the display frame 16 includes a recess 42. The recess 42 is a square depression defined by four side walls and a bottom wall 44. The recess 42 gives the display frame 16 the appearance of a picture frame surrounding and framing the bottom wall 44 of the recess 42. FIG. 7, which shows a cross sectional view of the dispensing system 10, shows side walls defining the recess 42 having steps or curves 46 in the manner of an ornate picture frame. The recess 42 is centered in the front face 38 and is disposed away from the side walls 36. The front face 38 appears as a border extending around the edges that define the recess 42, wherein the front face 38 has a constant width within a range of about 5 mm (0.197 in.) to about 20 mm (0.787 in.). In a different embodiment, the front face 38 may be planar and devoid of a recess. In yet another embodiment, a single stepped recess is provided. In still another embodiment, a multiple stepped recess is provided. In any of the embodiments described herein, side walls defining the recesses may include curved and/or shaped walls. Further, in any of the embodiments described herein, a raised rib may extend about an outer periphery of the front face 38 adjacent side walls 36 of the display frame 16.

The rear face 40 of the display frame 16 includes a stepped recess 50 defined by stepped side walls and a square depression disposed therebetween. FIGS. 3 and 7 show that the stepped recess 50 is configured to completely receive the dispenser 12, with the dispenser 12 positioned so that the permeable membrane 24 surface is substantially flush with the rear face 40. The stepped recess 50 includes a shallow peripheral recess 52 and a deep central recess 54. The central recess 54 is configured and dimensioned to receive the cup-shaped structure 26, and the peripheral recess 52 is configured and dimensioned to receive and support the flange 20. The central recess 54 and the peripheral recess 52 combined have a negative shape that is the same as that of the dispenser 12.

The peripheral recess 52 in one embodiment has a mechanical and/or adhesive retaining means (not shown) that is configured to hold the flange 20 in place. The flange 20 and the stepped side walls defining the peripheral recess 52 may be adhered to one another through the use of any adhesive, or alternately through a mechanical means, such as an interference fit, or a separate mechanical fastener, such as a spring clip. Further, a pair of magnets having opposing polarity or a magnet in combination with a ferritic material could also be utilized to hold the flange 20 adjacent the stepped side walls of the peripheral recess 52. When an adhesive is used, a flange-to-frame adhesive may be chosen to either permanently adhere the flange 20 to the display frame 16 or, alternately, be releasably adhered for easy removal. In this manner, the display frame 16 can be a permanent and reusable item to which a succession of replacement dispensers 12 are affixed and later removed and replaced. An ultra violet (UV) cured adhesive may also be used.

As may be seen in FIG. 7, the central recess 54 is deeper than the peripheral recess 52 since it must accommodate the greater combined thickness of the cup-shaped structure 26, the flange 20 and the permeable membrane 24. The bottom wall 28 of the cup-shaped structure 26 is adjacent to and slightly spaced apart from a bottom 56 of the central recess 54. The central recess 54 and the peripheral recess 52 are centrally spaced from the edges of the rear face 40.

The rear face 40 of the display frame 16 also includes a curved foot 58 disposed adjacent a lower side 60 of the display frame 16. The lower side 60 of the display frame 16 is defined by one of the side walls 36 that rests against a support surface. The curved foot 58 increases the stability of the display frame 16 to prevent same from tipping over. However, should the display frame 16 be tipped over, the curved foot 58 causes the permeable membrane 34 to be spaced from the support surface so that the potential for damage to the support surface by the volatile material 32 is minimized. The curved foot 58 extends outwardly from the rear face 40 about 4 mm (0.157 in.) to about 7 mm (0.276 in.) at its farthest point.

Figure 10:
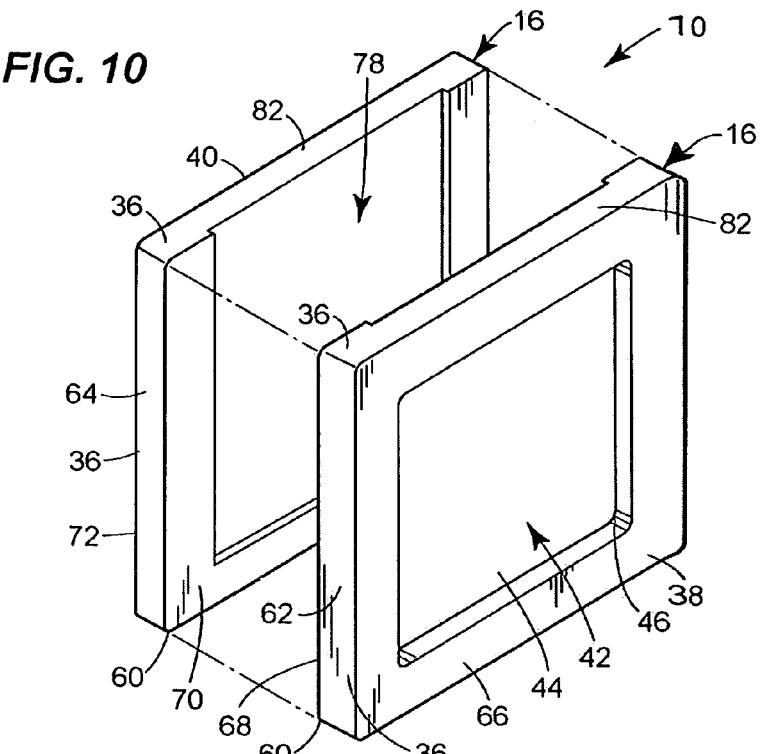
FIG. 10 is an exploded front isometric view of front and rear blocks comprising a frame.
Figure 11:
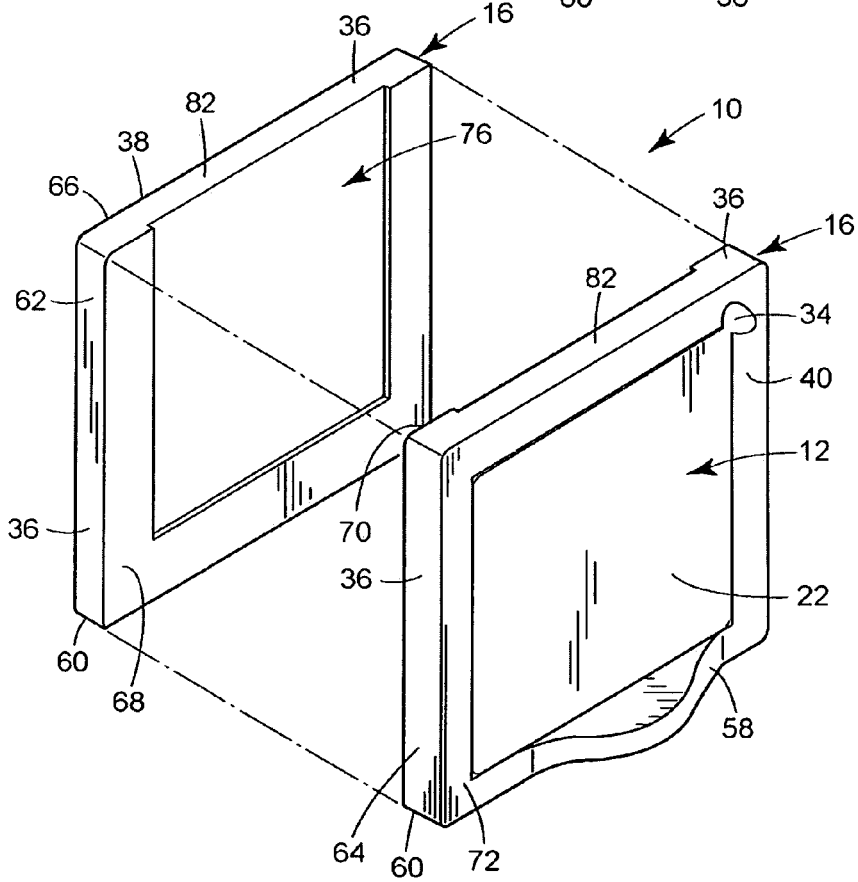
FIG. 11 is an exploded rear isometric view of the frame of FIG. 10.

With particular reference to FIGS. 10 and 11, it is shown that the display frame 16 may be formed by bonding front and rear blocks 62, 64 together. The front block 62 includes a front panel 66 commensurate with the position and size of the front face 38 and a rear panel 68. Similarly, the rear block 64 includes a front panel 70 and a rear panel 72 commensurate with the position and size of the rear face 40. The front and rear blocks 62, 64 have length and width dimensions equal to about those of the display frame 16. Further, the combined thickness of the front and rear blocks 62, 64 equals about the thickness of the display frame 16. The rear panel 68 of the front block 62 is joined with the front panel 70 of the rear block 64 to make the display frame 16, wherein the front and rear blocks 62, 64 are joined at seam 74.

A first recess 76 is formed into the rear panel 68 of the front block 62. The recess 76 is defined by a rectangular depression that extends from one of the side walls 36 to an area adjacent an opposing side wall 36. Similarly, a second recess 78 is formed into the front panel 70 of the rear block 64 that is sized and aligned with the first recess 76. When the first and second blocks 62, 64 are joined, the first and second recesses 76, 78 are aligned with one another to form a single slot 80 configured to hold and/or display the decorative element, which may be an image such as a photograph, a picture, and/or a drawing. Alternatively, a single recess having the same thickness as the combined first and second recesses 76, 78 may be formed in either the rear panel 68 of the front block 62 or the front panel 70 of the rear block 64. In this embodiment, the slot 80 is disposed on a top side 82 of the frame 16, wherein the top side 82 is defined by one of the side walls 36. Slot 80 defines a void having a height within a range of about 60 mm (2.362 in.) to about 100 mm (3.937 in.), a width within a range of about 50 mm (1.969 in.) to about 80 mm (3.150 in.), and a thickness within the range of about 1 mm (0.039 in.) to about 5 mm (0.197 in.). More particularly, the slot 80 is sized to allow any decorative element 14 to be removably inserted therein by a user and may comprise any suitable height, width, and thickness proportions necessary to accommodate the decorative element 14. For example, in one embodiment the slot may have a height and width within a range of about 10 mm (0.394) to about 500 mm (19.685 in.), and more particularly within a range of about 20 mm (0.787 in.) to about 250 mm (9.843 in.), and most particularly within a range of about 40 mm (1.575 in.) to about 125 mm (4.921 in.).

The display frame 16 may be constructed from a variety of compositions, including glass or an injection-molded plastic such as a copolyester resin. Illustratively, the display frame 16 is constructed from molded glass that is clear and/or transparent. The decorative element 14 is therefore viewable through the transparent front face 38 of the display frame 16. Furthermore, if the decorative element 14 is removed from the slot 80, the cup-like structure 26 is viewable through the transparent front face 38. As noted above, the cup-like structure 26 may be clear and translucent, allowing for the visibility of the volatile material 32 contained within the blister 18.

Figure 12:
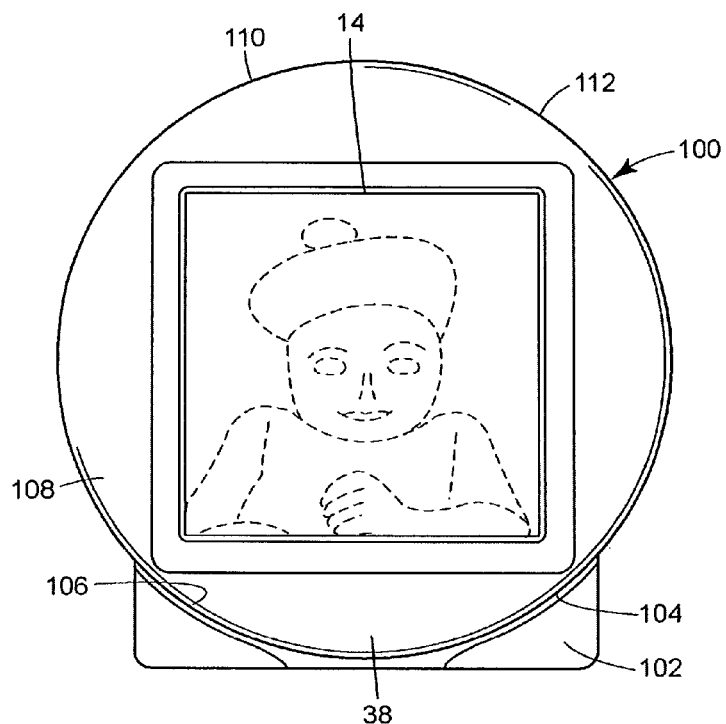
FIG. 12 is a front elevational view of a second embodiment of the dispensing system.
Figure 14:
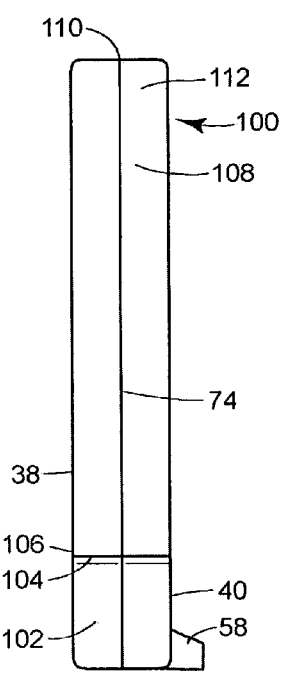
FIG. 14 is a side elevational view of the dispensing system of FIG. 12.
Figure 13:
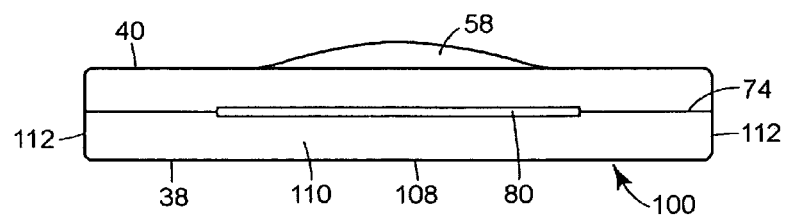
FIG. 13 is a plan view of the dispensing system of FIG. 12.

A second embodiment of the dispensing system 10 is depicted in FIGS. 12-14. The second embodiment is similar to the previously described first embodiment except that the second embodiment includes a frame 100 having a non-rectangular shape and a planar front face 38 devoid of the recess 42. Alternatively, the front face 38 of the present embodiment, and those discussed herein, may include a stepped recess disposed within the front face 38. The frame 100 includes a rectangular base 102 having a width of about 76 mm (2.992 in.) and a thickness of about 16 mm (0.630 in.). The base 102 has a rounded recess 104 disposed on a top side thereof that is contoured to interfit with a lower portion 106 of a circular body 108. The circular body 108 is integral with the base 102 and has a diameter of about 102 mm (4.016 in.). The combined height of the integral base 102 and the circular body 108 is about 103 mm (4.055 in.). The slot 80 is disposed in an upper portion 110 of a uniform side wall 112 spanning the distance between the front and rear faces 38, 40.

Figure 15:
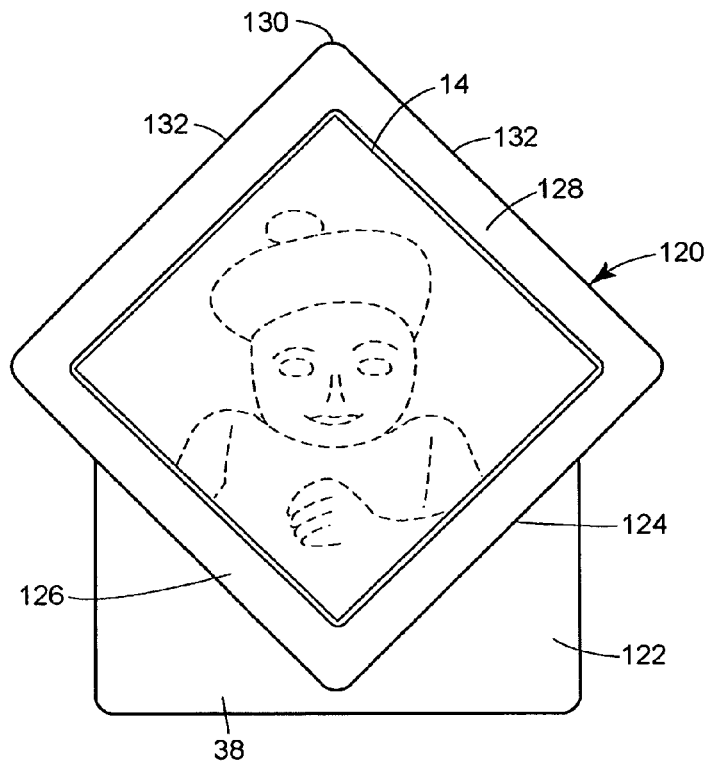
FIG. 15 is a front elevational view of a third embodiment of the dispensing system.
Figure 16:
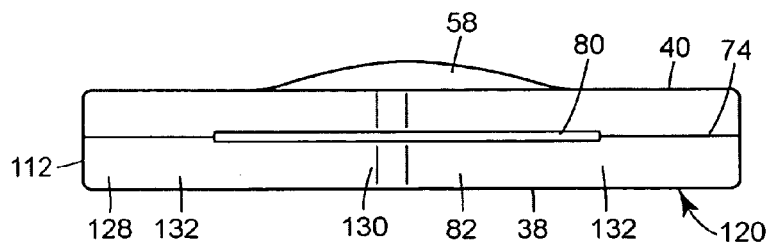
FIG. 16 is a plan view of the dispensing system of FIG. 15.
Figure 17:
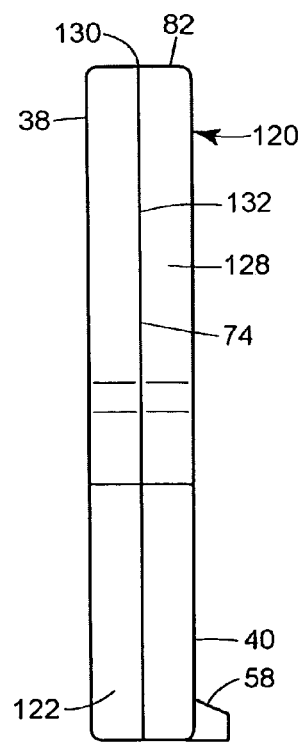
FIG. 17 is a side elevational view of the dispensing system of FIG. 15.

A third embodiment of the dispensing system 10 is depicted in FIGS. 15-17. Similar to the second embodiment, the third embodiment differs from the first embodiment in that a frame 120 comprises a non-rectangular structure and has a planar front face 38 devoid of the recess 42. The frame 120 includes a rectangular base 122 having a width of about 76 mm (2.992 in.) and a thickness of about 16 mm (0.630 in.). The rectangular base 122 has a triangular recess 124 disposed in a top side thereof that is contoured to interfit with a lower portion 126 of a diamond shaped body 128. The diamond shaped body 128 is integral with the rectangular base 122 and has a width (defined as the distance between opposing edges of the diamond shaped body 128) of about 103 mm (4.055 in.). The combined height of the integral rectangular base 122 and the diamond shaped body 128 is about 107 mm (4.213 in.). The slot 80 is disposed on an upper portion 130 that spans two side walls 132 of the frame 120.

Figure 18:
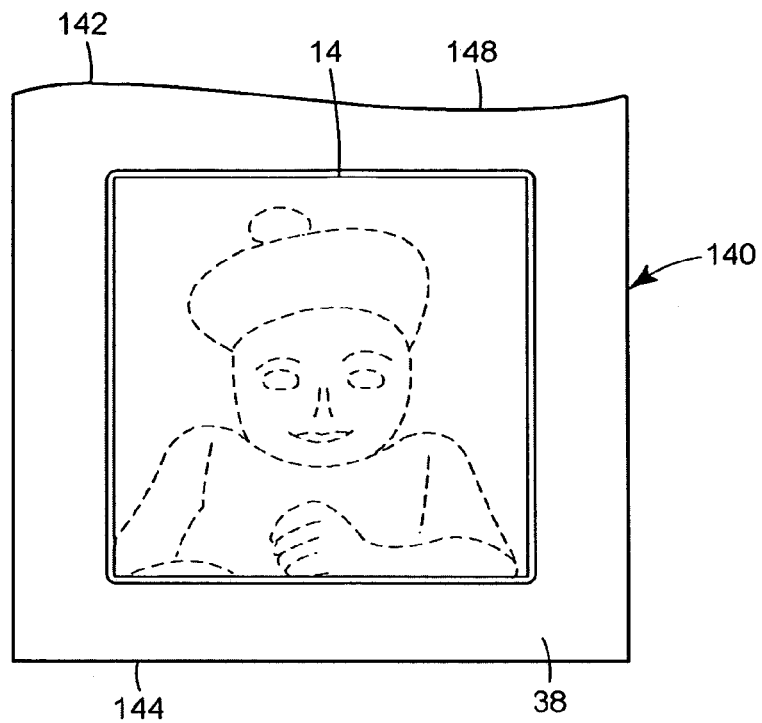
FIG. 18 is a front elevational view of a fourth embodiment of the dispensing system.
Figure 19:
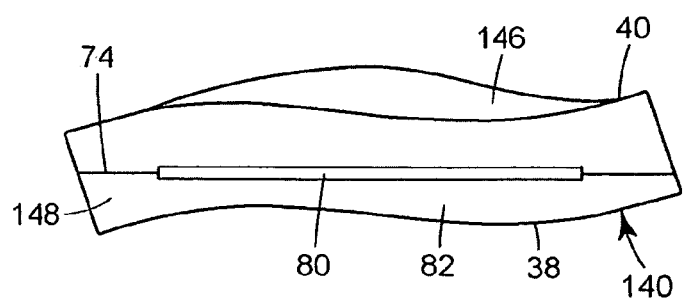
FIG. 19 is a plan view of the dispensing system of FIG. 18.
Figure 20:
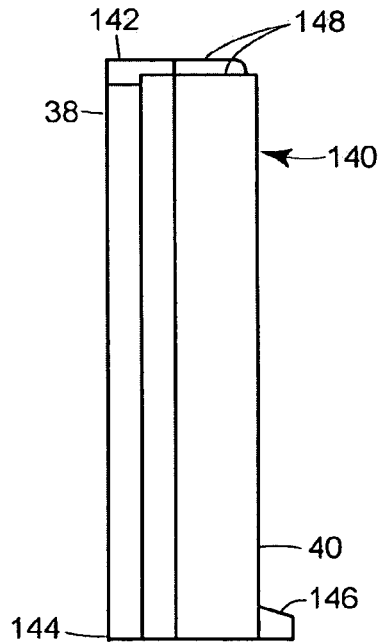
FIG. 20 is a side elevational view of the dispensing system of FIG. 18.

A fourth embodiment of the dispensing system 10 is shown in FIGS. 18-20 depicting a frame 140. The fourth embodiment differs from the first embodiment by way of having a non-rectangular frame 140 and a front face 38 devoid of the recess 42. The frame 140 comprises a wave-like shape. The wave-shaped frame 140 has a constant thickness of about 16 mm (0.630 in.), but curves inwardly and outwardly throughout the approximate 85 mm (3.346 in.) width of the wave shaped frame 140. The height of the wave shaped frame 140 is not constant because an upper portion 142 thereof has a wave-shaped appearance. However, a peak height of the wave shaped frame 140, measured from a lower portion 144 to the upper portion 142, is about 86 mm (3.386 in.). Further, the wave shaped frame 140 differs from the first embodiment in that the wave shaped frame 140 includes a wave-shaped foot 146 on the rear face 38 that differs from the curved foot 56 of the first embodiment. The combined thickness of the wave shaped frame 140 and the foot 146, measured between points that extend the farthest outwardly from both the front and rear faces 36, 38, is about 25 mm (0.984 in.). The slot 80 is disposed in a top side 148 of the wave shaped frame 140.

Figure 21:
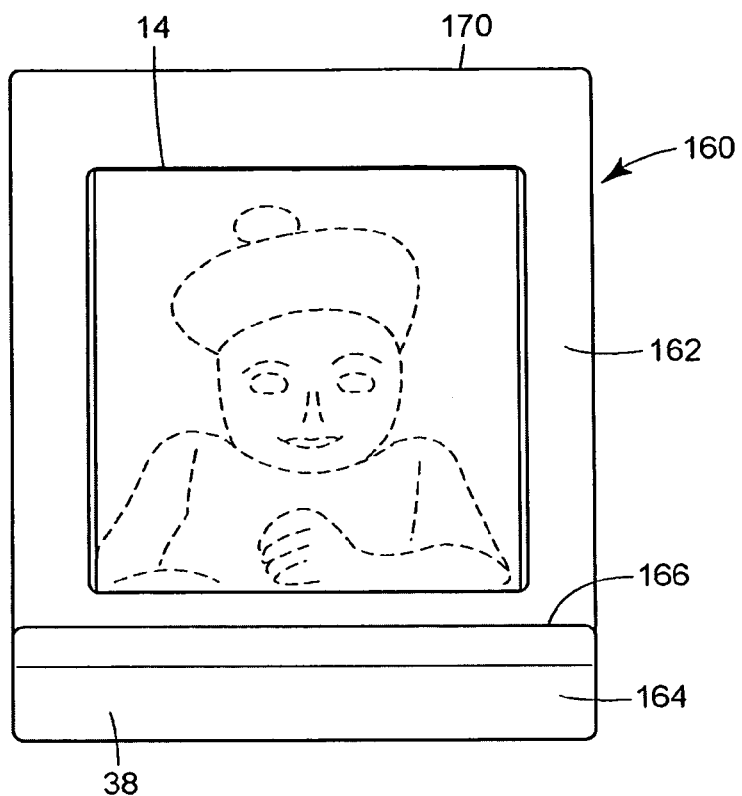
FIG. 21 is a front elevational view of a fifth embodiment of the dispensing system.
Figure 22:
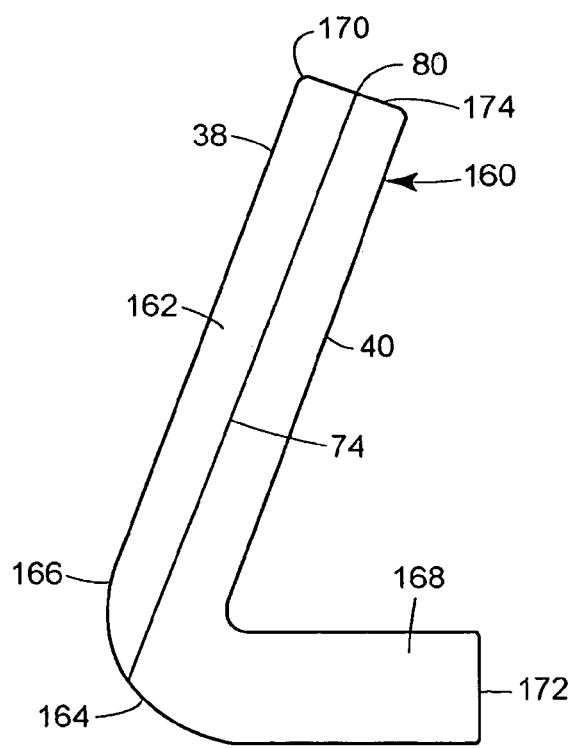
FIG. 22 is a side elevational view of the dispensing system of FIG. 21.

A fifth embodiment of the dispensing system 10 is shown in FIGS. 21 and 22 that differs from the first embodiment only with respect to the display frame 16. The fifth embodiment includes a frame 160 that has a rectangular body 162. The rectangular body 162 is integrally connected to a curvilinear portion 164 on a lower portion 166 thereof. The curvilinear portion 164 is also integrally connected to a rectangular base 168. The rectangular body 162 is not perpendicular with respect to the rectangular base 168, but rather is deflected toward the rectangular base 168. The frame 160 has a width of about 80 mm (3.150 in.) and a height of about 96 mm (3.780 in.), wherein the height is measured from the rectangular base 168 to an upper portion 170 of the rectangular body 162. The frame 160 has a thickness of about 51 mm (2.008 in.), which is measured from an area of the curvilinear portion 164 adjacent the rectangular body 162 to an end 172 of the rectangular base 168. The slot 80 is disposed on a top side 174 of the frame 160.

Figure 23:
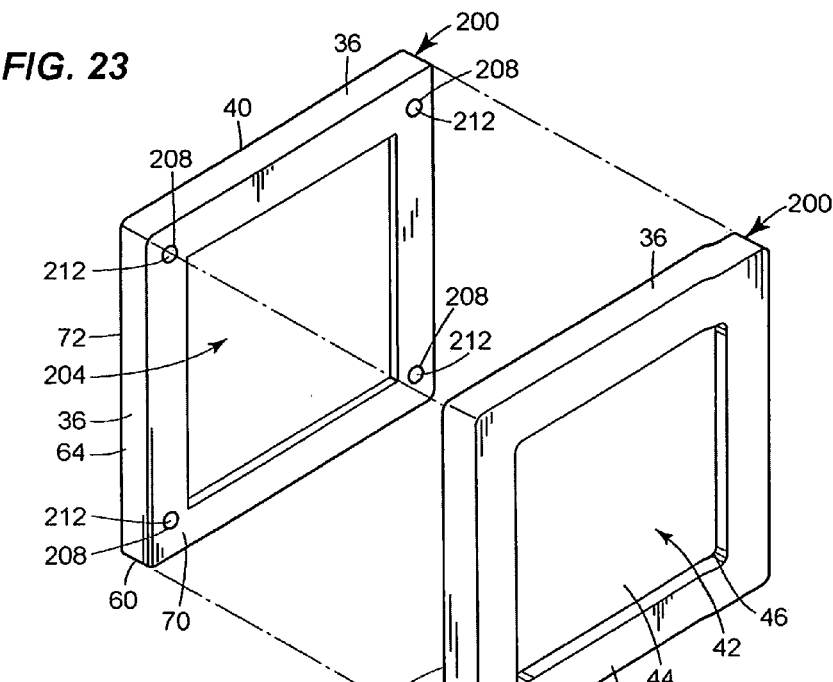
FIG. 23 is an exploded front isometric view of a sixth embodiment of the dispensing system showing separated front and rear blocks of a frame.
Figure 24:
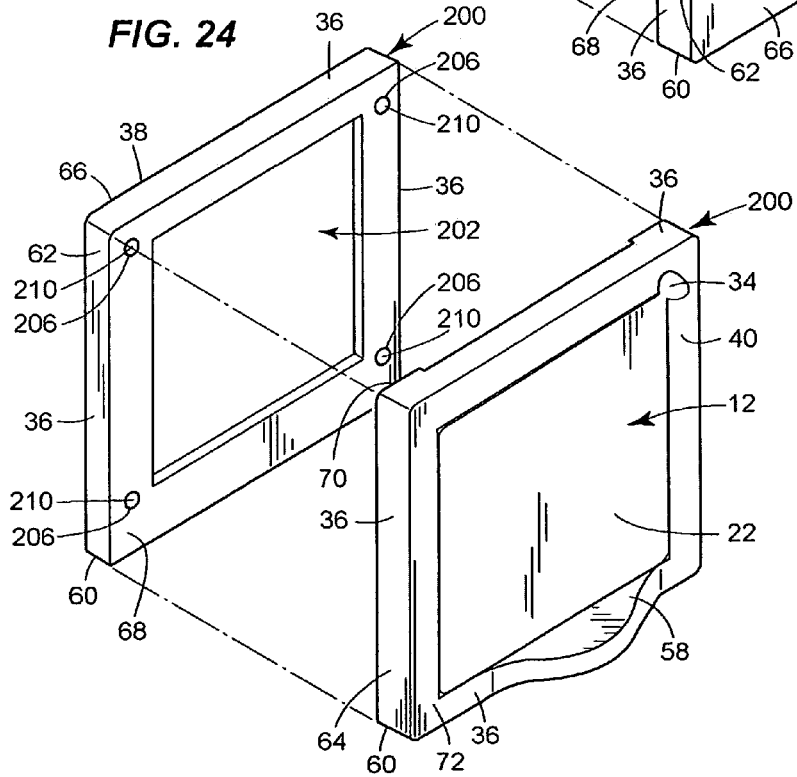
FIG. 24 is an exploded rear isometric view of the dispensing system of FIG. 23 showing separated front and rear blocks of the frame.
Figure 25:
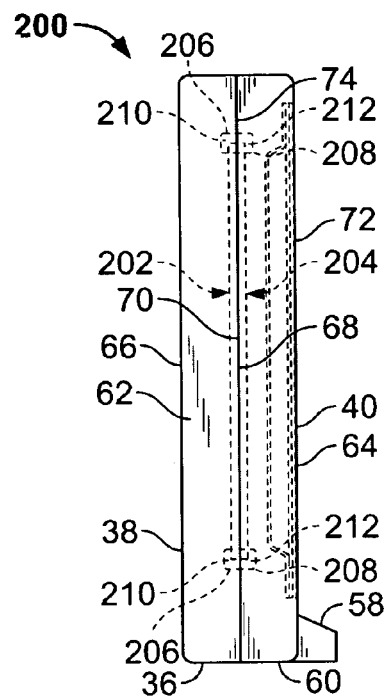
FIG. 25 is a side elevational view of the assembled dispensing system of FIG. 23.

Referring to FIGS. 23-25, a sixth embodiment of the volatile material dispensing system 10 that includes a frame 200 is illustrated. The present embodiment is similar to the first embodiment except that the frame 200 of the present embodiment does not have permanently bonded front and rear blocks 62, 64. Rather, the front and rear blocks are held together by removable attachment means such as a mechanical fastener, an adhesive, and/or magnets.

FIGS. 23 and 24 depict the front block 62 with the front and rear panels 66, 68 and the rear block 64 with the front and rear panels 70, 72. Further, a first recess 202 is provided in the rear panel 68 of the front block 62 and a second recess 204 is provided in the front panel 70 of the rear block 64. Alternatively, a single recess having the same thickness as the combined first and second recesses 202, 204 may be formed in either the rear panel 68 of the front block 62 or the front panel 70 of the rear block 64. The first and second recesses 202, 204 are defined by centrally disposed rectangular depressions that do not extend to the outer periphery of the front and rear blocks 62, 64. The first and second recesses 202, 204 have length and width dimensions within the range of about 50 mm (1.969 in.) to about 70 mm (2.756 in.).

A circular depression 206 is disposed adjacent each corner of the rectangular recess 202 on the rear panel 68. Similarly, circular depressions 208 are provided at each corner of the second recess 204 on the front panel 70. Magnets 210, 212 are positioned within each of the circular depressions 206, 208, respectively. The magnets 210, 212 are retained within the circular depressions 206, 208 by means of an adhesive and/or by a press-fit. The magnets 210, 212 include top portions that are substantially level with respect to the rear and front panels 68, 70. The magnets 210 on the rear panel 68 have an opposite polarity to the magnets 212 on the front panel 70. In an alternative embodiment, at least one of the magnets 210 is replaced by a ferritic material within the circular depression 206 and opposite the respective magnet 212.

The decorative element 14 is inserted into either the first or second recess 202, 204 so that a side to be viewed is closer to the front face 36 of the frame 200. As may be seen in FIG. 25, the front and rear blocks 62, 64 are thereafter pressed together so as to align the front and rear recesses 202, 204 and the magnets 210, 212. The magnets 210, 212 retain the front and rear blocks 202, 204 together to form a unified frame 200 that may be easily separated to change the decorative element 14.

A seventh embodiment of the volatile material dispensing system 10 is depicted in FIGS. 26-37. The seventh embodiment includes a display frame 300 similar to the first embodiment except that the display frame 300 does not comprise separately bonded front and rear blocks 62, 64. Rather, the display frame 300 comprises a uniform block with four substantially equal-sized side walls, a front face 302, and a rear face 304. The four side walls comprise a substantially planar bottom wall 306 and substantially curvilinear left, right, and top walls 308, 310, 312, respectively. The curvilinear left wall 308, right wall 310, and top wall 312 include a central portion 314 that extends outwardly from the display frame 300 to a greater extent than opposing ends of the respective walls 308-312. Further, the left and right walls 308, 310 and the top wall 312, are angled inwardly and downwardly, respectfully, as the walls 308-312 extend from the front face 302 of the display frame 300 toward the rear face 304 thereof. In one embodiment, the display frame 300 has a thickness between the front and rear faces 302, 304 within a range of about 12 mm (0.472 in.) to about 22 mm (0.866 in.), or within a range of about 15 mm (0.591 in.) to about 19 mm (0.748 in.). The display frame 300 may also have a height between the central portion 314 of the top wall 312 and the bottom wall 36 within a range of about 60 mm (2.362 in.) to about 110 mm (4.331 in.), or within a range of about 72 mm (2.835 in.) to about 98 mm (3.858 in.). Similarly, the display frame 300 may have a width between the central portions 314 of the left and right walls 308, 310 within a range of about 60 mm (2.362 in.) to about 110 mm (4.331 in.), or within a range of about 72 mm (2.835 in.) to about 98 mm (3.858 in.).

Figure 26:
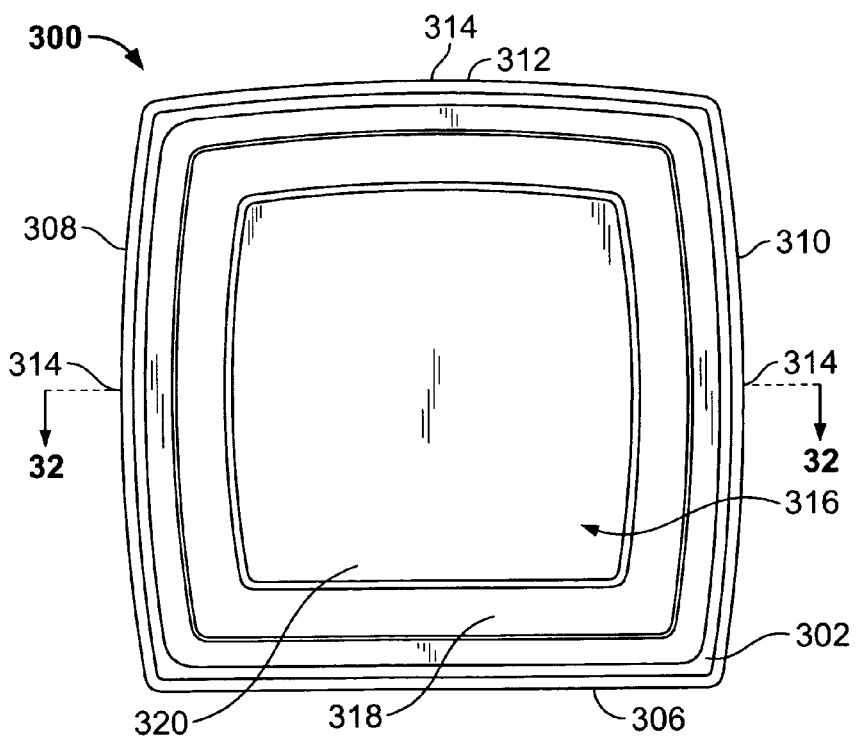
FIG. 26 is a front elevational view of a seventh embodiment of the dispensing system.

The front face 302 or front side of the display frame 300 includes a recess 316. FIG. 26 illustrates that the recess 316 is defined by four angled and curved side walls 318 and a bottom wall 320. The four side walls 318 have a shape substantially similar to the shape defined by one of the adjacent bottom, left, right, and top walls 306-312, i.e., the side wall 318 adjacent the bottom wall 306 is planar and parallel to same and each of the remaining three side walls 318 is curvilinear and parallel to one of the left, right, and top walls 308-312 adjacent thereto. The recess 316 is centered in the front face 302 of the display frame 300 and gives the display frame 300 the appearance of a picture frame surrounding the bottom wall 320 of the recess 316. The curved side walls 318 may include any number of angles and/or curves that may be symmetrical with the respective bottom, left, right, and top walls 306-312. However, other embodiments may include no recess, or multiple stepped recesses, or any other type of shaped side wall. In one embodiment, a raised rib extends about an outer periphery of the front face 302 adjacent the bottom, left, right, and top walls 306-312 of the display frame 300.

Figure 27:
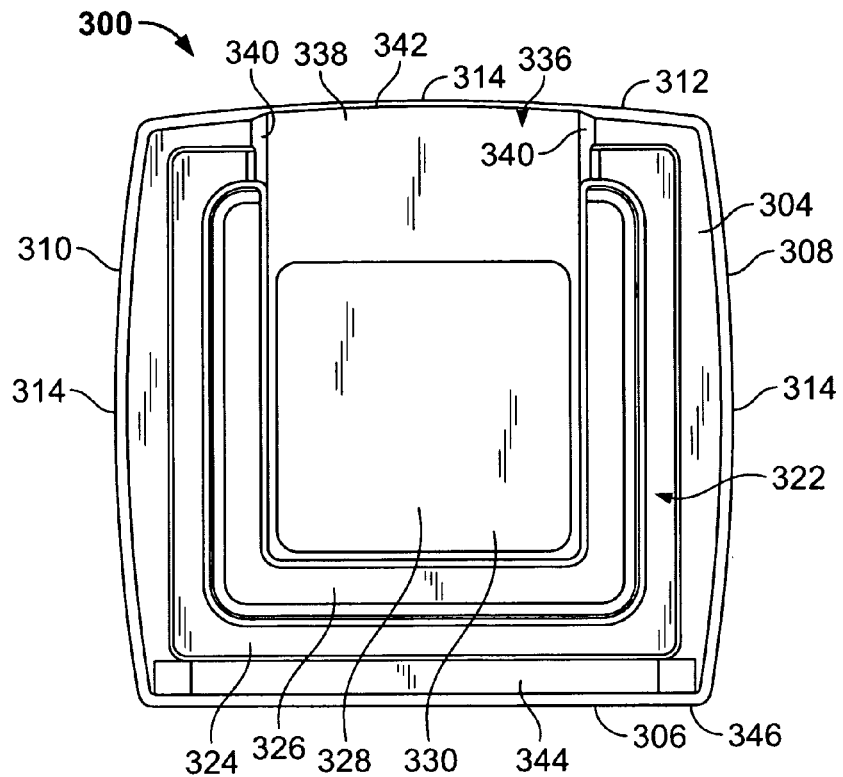
FIG. 27 is a rear elevational view of the dispensing system of FIG. 26.
Figure 28:
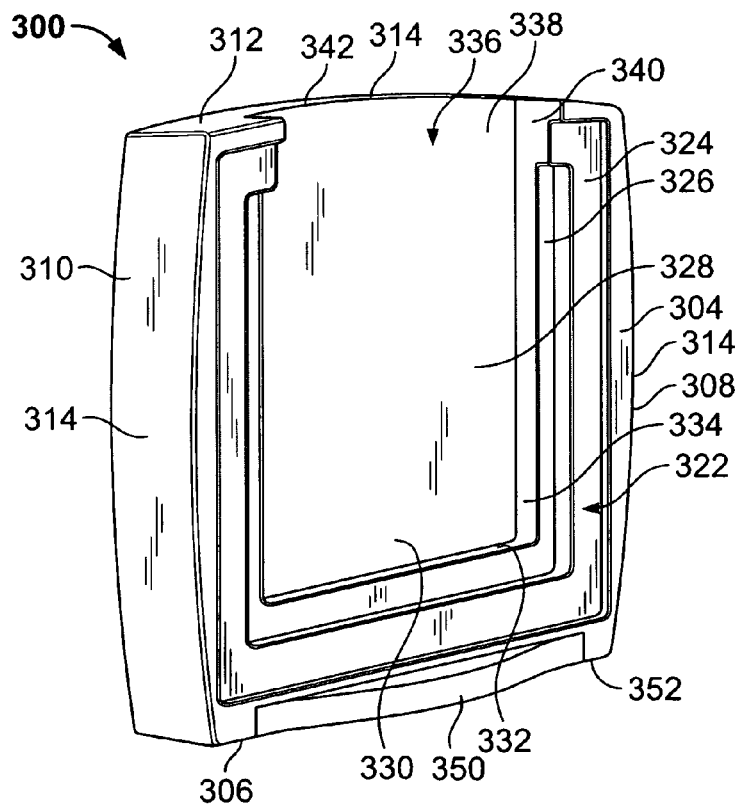
FIG. 28 is a rear isometric view of the dispensing system of FIG. 26.
Figure 29:
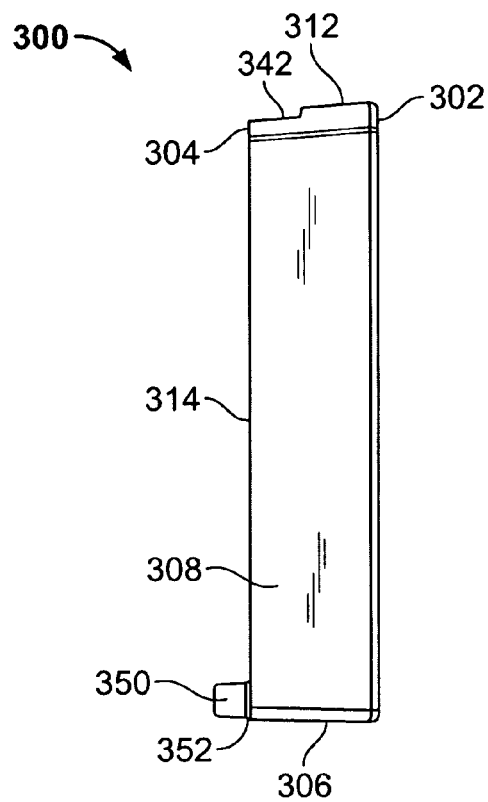
FIG. 29 is a side elevational view of the dispensing system of FIG. 26.
Figure 30:
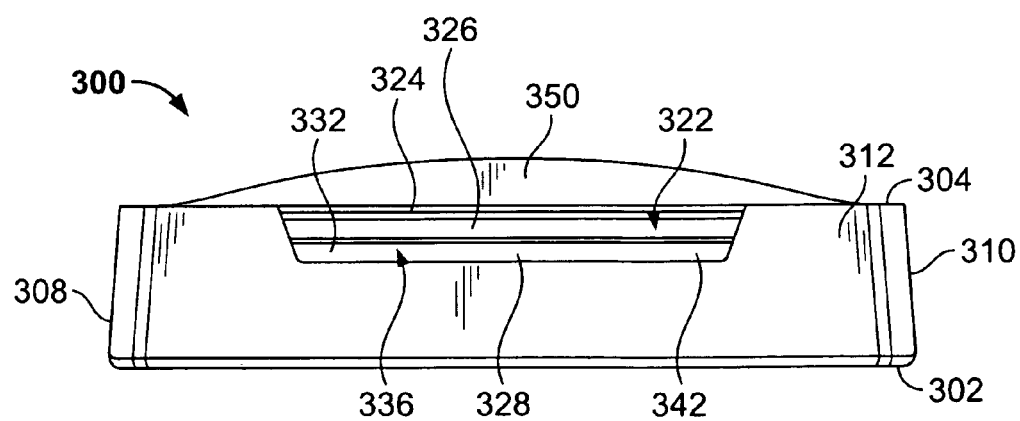
FIG. 30 is a plan view of the dispensing system of FIG. 26.
Figure 31:
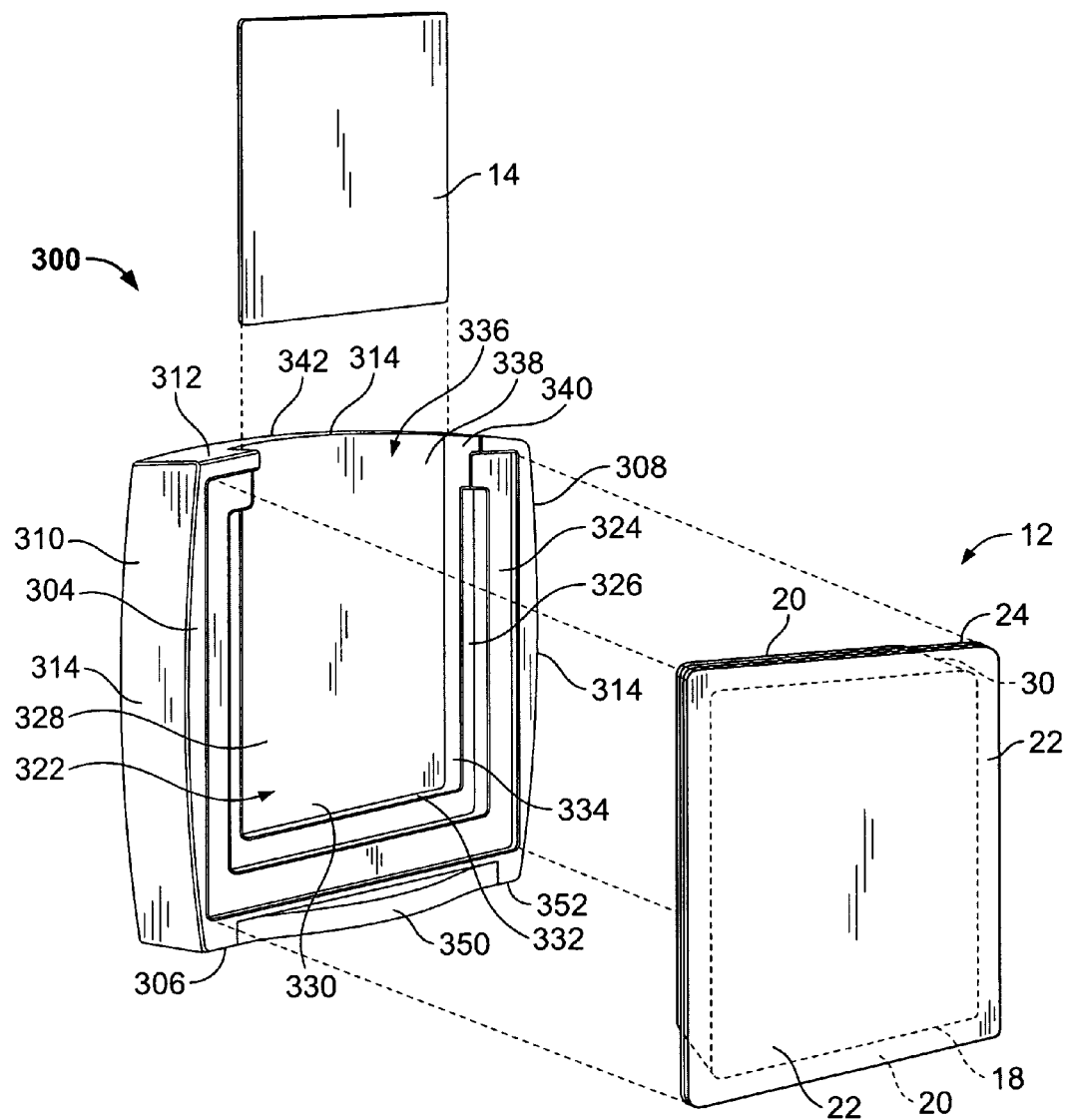
FIG. 31 is an exploded rear isometric view of the dispensing system of FIG. 26 depicting the display frame and a decorative element and a dispenser.

FIGS. 27, 28, and 31 show that the rear face 304 or rear side of the display frame 300 includes a stepped recess 322 defined by stepped side walls and a square depression disposed therebetween. The stepped recess 322 comprises a peripheral outer recess 324 and a medial recess 326 similar to the shallow peripheral recess 52 and the deep central recess 54, respectively, of the first embodiment. The stepped recess 322 also includes an inner recess 328.

Figure 32:
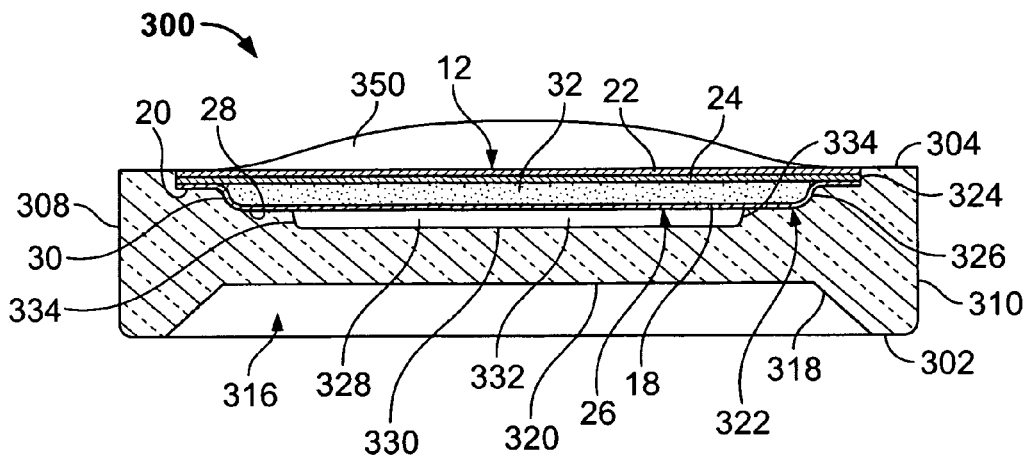
FIG. 32 is a cross-sectional view of the dispensing system taken along the line 32-32 of FIG. 26 further including a dispenser.

The peripheral outer recess 324 is configured and dimensioned to receive the support flange 20 of the dispenser 12. The medial recess 326 and the outer peripheral recess 324 combined have a negative shape that is the same as that of the dispenser 12. Alternatively, the medial recess 326 and the outer peripheral recess 324 may have a combined shape similar to that of any other volatile material holder that is to be positioned within the display frame 300. When the dispenser 12 is inserted into the stepped recess 322, such as is shown in FIG. 32, the dispenser 12 is completely received within the medial recess 326 and the peripheral outer recess 324 so that the permeable membrane 24 surface is substantially flush with the rear face 304 and the flange 20 rests upon the stepped side walls defining the peripheral outer recess 324. The flange 20 is adhered to the stepped side walls defining the peripheral outer recess 324 in a similar manner as described herein with respect to the other embodiments.

In this embodiment, the medial recess 326 is configured and dimensioned to receive the cup-shaped structure 26 of the dispenser 12. As may be seen in FIGS. 31 and 32, the medial recess 326 is deeper than the peripheral outer recess 324 since it accommodates the greater combined thickness of the cup-shaped structure 26, the flange 20, and the permeable membrane 24. Peripheral portions of the bottom wall 28 of the dispenser 12 are adjacent to and in contact or slightly spaced from the stepped side walls defining the medial recess 326. The bottom wall 28 of the dispenser 12 is also spaced from a bottom surface 330 of the stepped recess 322 by the inner recess 328.

Figure 33:
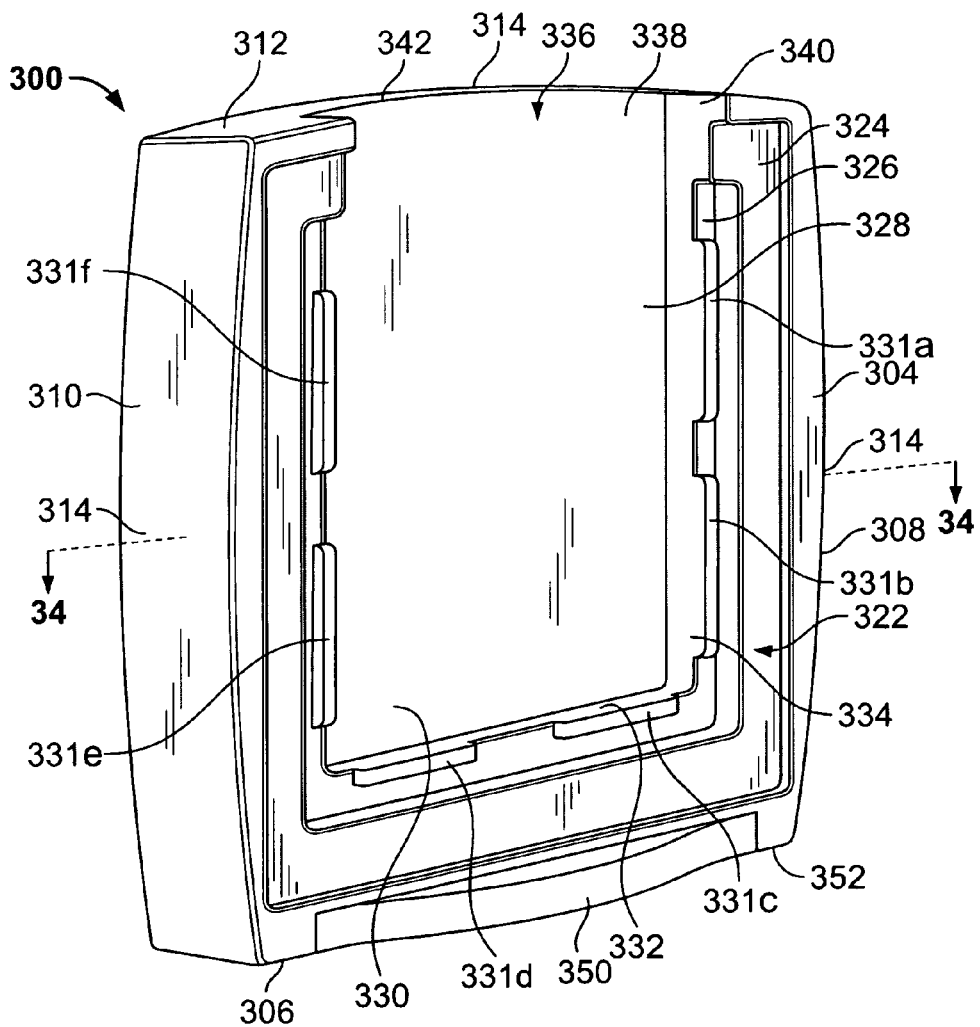
FIG. 33 is a rear isometric view of the dispensing system similar to the one depicted in FIG. 28 further including several protrusions.
Figure 34:
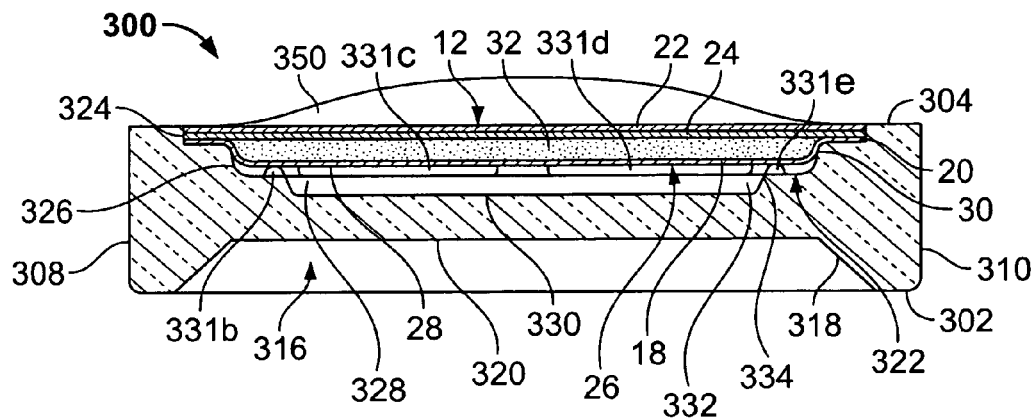
FIG. 34 is a cross-sectional view of the dispensing system taken along the lines 34-34 of FIG. 33 further including a dispenser.

FIGS. 33 and 34 depict an alternative embodiment of the display frame 300 where peripheral portions of the bottom wall 28 of the dispenser 12 are spaced from the stepped side walls of the medial recess 326. In the present embodiment, one or more spaced curved protrusions 331 are provided on the stepped side walls of the medial recess 326. The protrusions 331 fill a gap between the bottom wall 28 and the walls defining the medial recess 326. The protrusions 331 prevent the dispenser 12 from bending excessively or from breaking or becoming unattached to the display frame 300 when excessive force is exerted onto the dispenser 12. Excessive force may be a particular factor during the manufacturing process when the dispenser 12 is attached to the rear face 304 of the display frame 300. It is intended that other types of protrusions, whether singly or when one of a plurality, be considered within the scope of the present disclosure regardless of the protrusions geometric shape. The protrusions 331 may also provide enhanced decorative element retaining means by preventing vertical and/or lateral movement of the decorative element 14 from the confines of the inner recess 328, which will be described in further detail below.

FIGS. 31 and 32 illustrate that the inner recess 328 is configured and dimensioned to hold and/or display a decorative element 14 such as a photograph, a picture, and/or a drawing, to name a few. The inner recess 328 is substantially square and is defined by the bottom surface 330 and three equal sized walls comprising a bottom wall 332, and two side walls 334. FIGS. 27, 28, and 31 depict a top end of the inner recess that is open and coextensive with a channel 336 or slot. The channel 336 includes a bottom surface 338 that is planar with the bottom surface 330 of the inner recess 328 and two side channel walls 340 spaced from one another a similar distance as the opposing side walls 334 of the inner recess 328. The side channel walls 340 comprise a varying thickness as the channel extends from the top end of the of the inner recess 328 toward the top wall 312, i.e., the side channel walls 340 extend upwardly from the bottom surface 338 of the channel 336 a distance commensurate with the respective stepped side walls defining the medial and peripheral outer recesses 326, 324. The channel 336 extends through a portion of the top wall 312 and has an open end 342.

The channel 336 provides a user with means to insert the decorative element 14 into the inner recess 328 when the dispenser 12 is affixed to the rear face 304 of the display frame 300. A user first holds the decorative element 14, such as a photograph, above the channel 336 so that a viewing surface of the decorative element 14 is positioned toward the front face 302 of the display frame 300. The decorative element 14 is slid or otherwise inserted into the channel 336 between the bottom surface 338 of the channel 336 and the dispenser 12. The decorative element 14 thereafter is disposed partially or wholly within the inner recess 328.

In some embodiments, as noted above, peripheral portions of the bottom wall 28 of the dispenser 12 are spaced from the stepped side walls defining the medial recess 326, thereby creating a gap. In these embodiments, the decorative element 14 may slip or be otherwise moved from the inner recess 328 in a lateral (toward the left or right walls 308, 310, respectively, of the display frame 300) and/or in a longitudinal manner (toward the top or bottom walls 312, 306, respectively, of the display frame 300) and be offset into the gap. The protrusions 331 described in connection with FIGS. 33 and 34, and the intended variations thereof, provide a further functional characteristic by preventing longitudinal and/or lateral movement of the decorative element 14 from within the confines of the inner recess 328.

Figure 35:
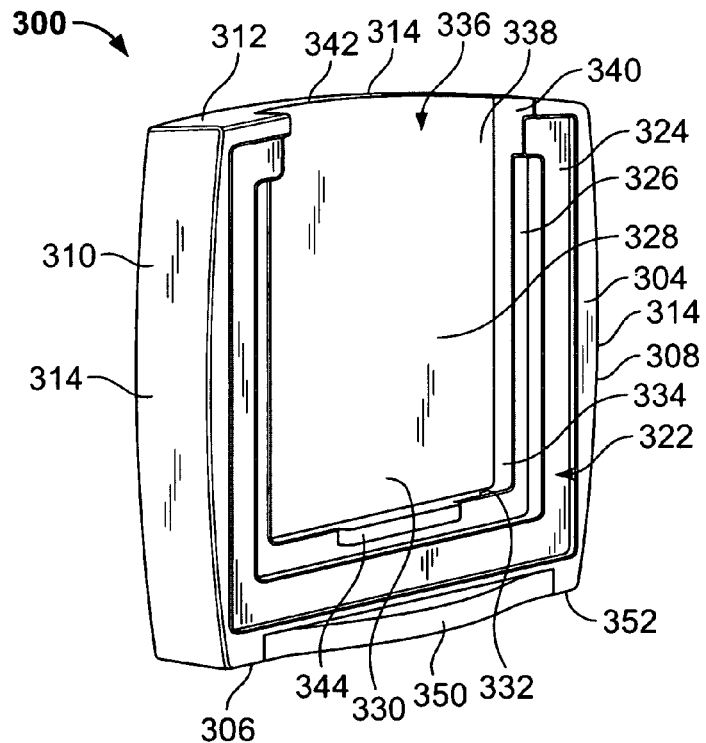
FIG. 35 is a rear isometric view of the dispensing system similar to the one depicted in FIG. 28 further including a raised bar.
Figure 36:
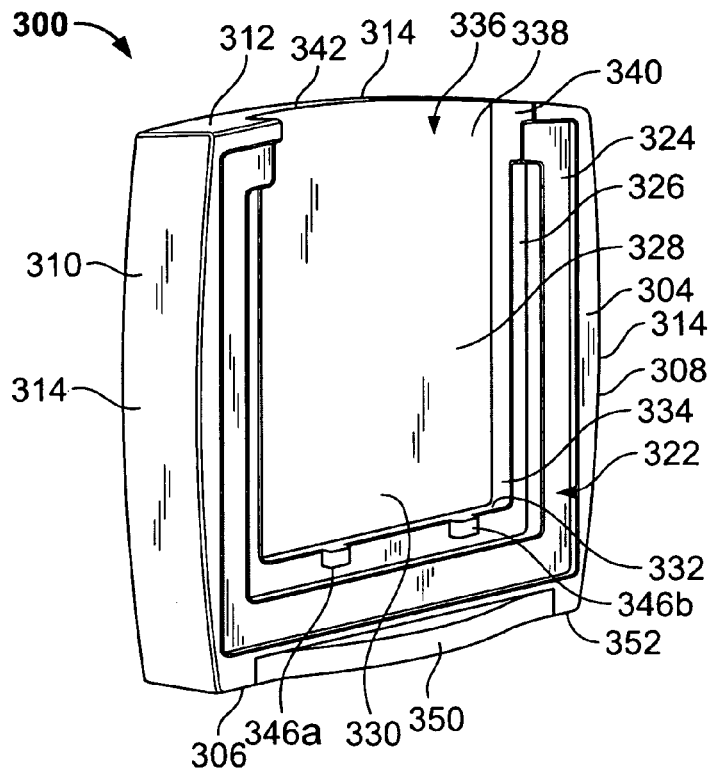
FIG. 36 is a rear isometric view of the dispensing system similar to the one depicted in FIG. 28 further including two raised bumps.
Figure 37:
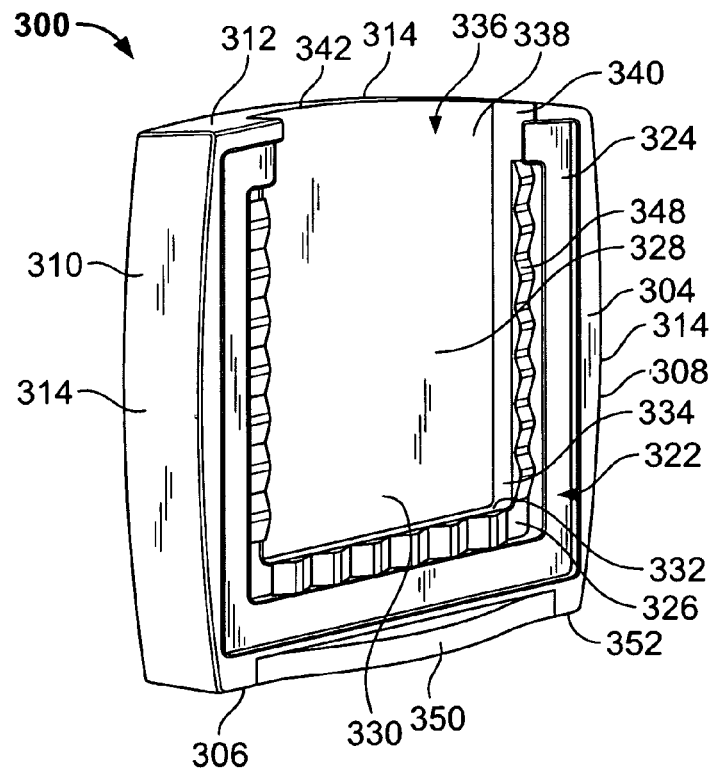
FIG. 37 is a rear isometric view of the dispensing system similar to the one depicted in FIG. 28 further including a plurality of upraised portions.

FIG. 35 depicts an alternative embodiment for preventing longitudinal movement of the decorative element 14 in a direction toward the bottom wall 306. A raised bar 344 is provided on a portion of the side wall defining the medial recess 326 adjacent the bottom wall 332 of the inner recess 328. The raised bar 344 fills the gap between the bottom wall 28 of the dispenser 12 and the side wall of the medial recess 326 to prevent the decorative element 14 from sliding downwardly and out of the inner recess 328. FIG. 36 depicts an embodiment similar to the one depicted in FIG. 35, except that the raised bar 344 is replaced by two raised bumps 346a, 346b to similarly prevent movement of the decorative element 14 into the gap between the bottom wall 28 and side walls defining the medial recess 326. In yet another embodiment depicted in FIG. 37, a plurality of upraised portions 348 is disposed on the side walls defining the medial recess 326 in a wave-like pattern. The upraised portions 348 are positioned to prevent lateral and/or longitudinal movement of the decorative element 14 from within the inner recess 328. Various structures with different geometric shapes are envisioned to be used in connection with the present embodiments, insofar as the structures assist in substantially preventing the decorative element 14 from moving out of the inner recess 328 and into portions of the medial recess 326. Further, any number of geometric structures positioned adjacent the bottom, left, right, or top walls 306-312 may be used. Still further, the geometric structures may provide the same functional characteristics as the protrusions 331 described above or may work in tandem with them.

In other embodiments of the display frame 300, the spacing between the bottom surface 338 and portions of the dispenser 12 may be sized to allow for varying widths of decorative elements by, for example, adjusting the size of one or more of the stepped side walls defining the stepped recess 322, making the channel 336 shallower, and/or adjusting the size of the dispenser 12. The bottom surface 330 of the inner recess 328 is similarly spaced from the bottom wall 28 of the dispenser 12 and may be modified to accommodate various sized decorative elements by adjusting the sizing of the stepped recess 322, the inner recess 328, and/or the dispenser 12. In a different embodiment, the spacing between the bottom surface 330 and the dispenser 12 is different than the spacing between the bottom surface 338 and the dispenser 12.

Adjusting the spacing between at least one of the bottom surfaces 330, 338 and the bottom wall 28 also provides for varying means of holding the decorative element 14 within the inner recess 328. In one embodiment, the spacing between the bottom surface 330 and the bottom wall 28 is relatively narrow so that when the decorative element 14 is inserted therebetween the decorative element 14 remains stationary and held in place by frictional forces. In another embodiment, the spacing similarly allows for a frictional fit that is easily disrupted by movement of the display frame 300. In a different embodiment, spacing is provided that is about the same or slightly larger than the width of the decorative element 14. Little or no frictional forces are therefore imparted to the decorative element 14 but the decorative element 14 still remains completely or substantially parallel to the bottom surface 330 of the inner recess 328. In yet anther embodiment, the spacing is substantially greater than the width of the decorative element 14, wherein placement of the decorative element 14 into the inner recess 328 may allow the decorative element 14 to slightly tilt or rotate therein. It is contemplated that the spacing between the bottom surface 330 and the bottom wall 28 may be adjusted for any type of decorative element, such as a photograph, picture, drawing, written document, or other aesthetic or functional types of information. Similarly, the spacing between the bottom surface 338 of the channel 336 and any portion of the dispenser 12 adjacent thereto may be adjusted if the decorative element 14 extends wholly or partially into the channel 336.

The decorative element 14 is removed from the display frame 300 by tilting, turning, and/or rotating the display frame 300 so that the open end 342 of the channel 336 is angled from its normal operating position. Angling the open end 342 of the channel 336 allows gravitational forces to independently, or in combination with forces from a user, remove the decorative element 14 from the display frame 300 through the open end 342. In other embodiments, a user may use a finger or other object to pull or grasp and remove the decorative element 14 from the display frame 300. In yet another embodiment, the decorative element 14 is removed by pulling the dispenser 12 off of the frame 300 to expose the inner recess 328 and the decorative element 14 therein.

The inner recess 328 is centered within the rear face 304 of the display frame 300. Centering the inner recess 328 allows the user to easily center the decorative element 14 to be disposed therein with respect to the bottom, left, right, and top walls 306-312 of the display frame 300. The length of the bottom and the two side walls 332, 334 of the inner recess 328 may be adjusted to accommodate various sized decorative elements. For example, the spacing between the two side walls 334 may be adjusted to be substantially equal to the width of the decorative element, thereby obviating the need to center the decorative element within the inner recess 328. In a different embodiment, the spacing between the two side walls 334 is adjusted to be greater than the width of the decorative element, thereby allowing a user to see the level of volatile material 32 about a periphery of the decorative element 14. The spacing between the bottom wall 332 and the top end of the inner recess 328 may likewise be adjusted to be substantially equal to or greater than the height of the decorative element. In a different embodiment, spacers (not shown) are provided that may be inserted into the inner recess 328 to position the decorative element. The spacers may be made of a similar or dissimilar material as the display frame 300 and may be colored or transparent.

The rear face 304 of the display frame 300 also includes a curved foot 350 or protrusion disposed adjacent a lower side 352 of the display frame 300. The lower side 352 of the display frame 300 is defined by the bottom wall 306 that rests against a support surface. The curved foot 350 increases the stability of the display frame 300 to prevent same from tipping over. However, should the display frame 300 be tipped over, the curved foot 350 causes the permeable membrane 34 to be spaced from the support surface so that the potential for damage to the support surface by the volatile material 32 is minimized. The curved foot 350 extends outwardly from the rear face 304 about 4 mm (0.158 in.) to about 7 mm (0.276 in.) at its farthest point.

Figure 38:
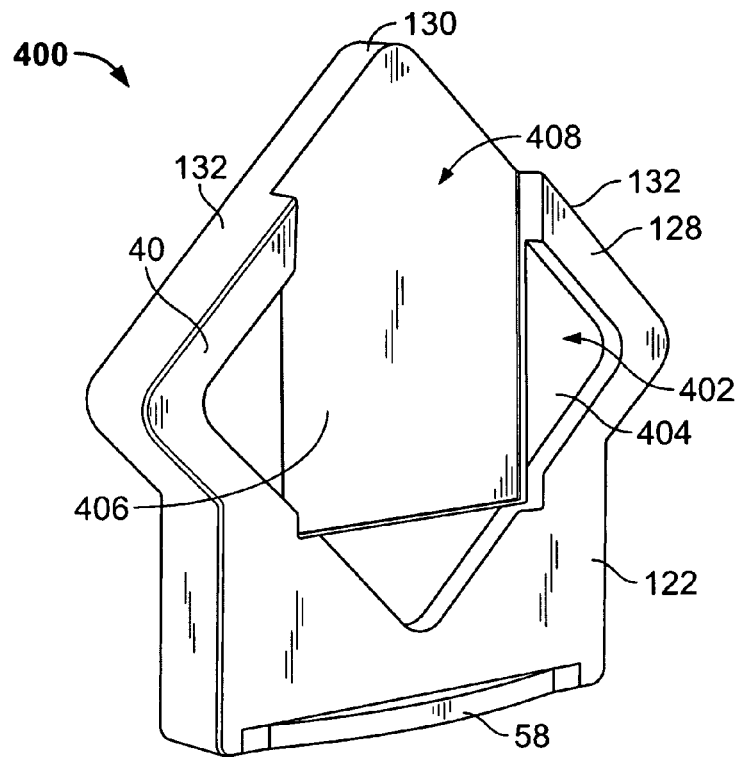
FIG. 38 is a rear isometric view of an eighth embodiment of the dispensing system similar to the third embodiment depicted in FIGS. 15-17 that further includes a stepped recess and omits the slot.
Figure 39:
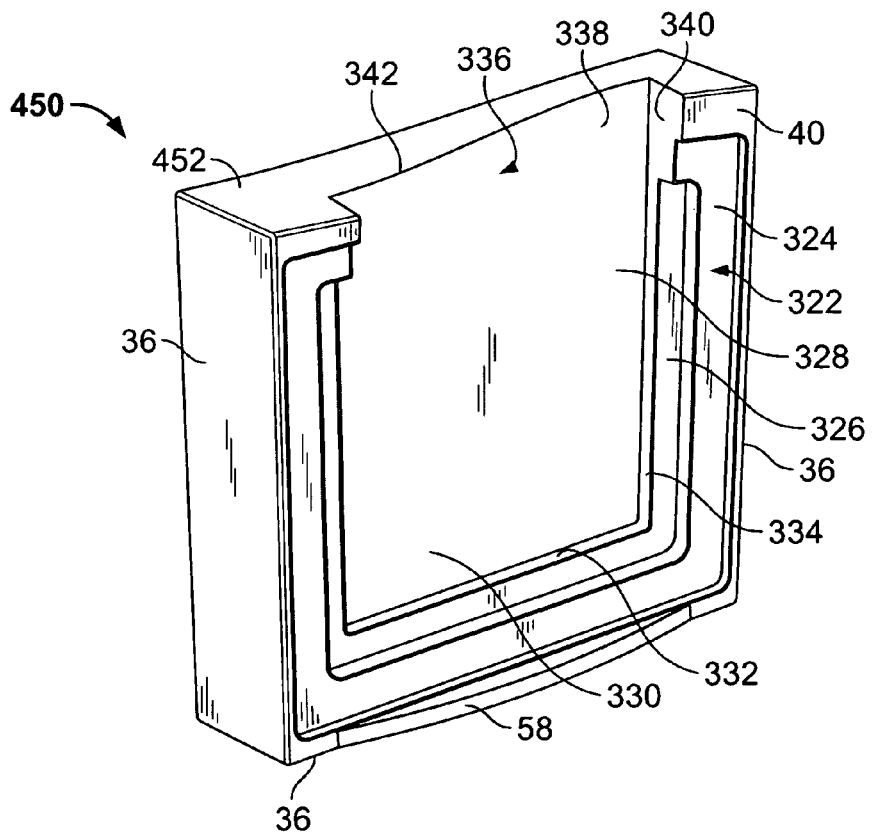
FIG. 39 is a rear isometric view of a ninth embodiment of the dispensing system similar to the first embodiment depicted in FIGS. 1-7 and the fourth embodiment depicted in FIGS. 18-20 that further includes a stepped recess and omits the slot.
Figure 40:
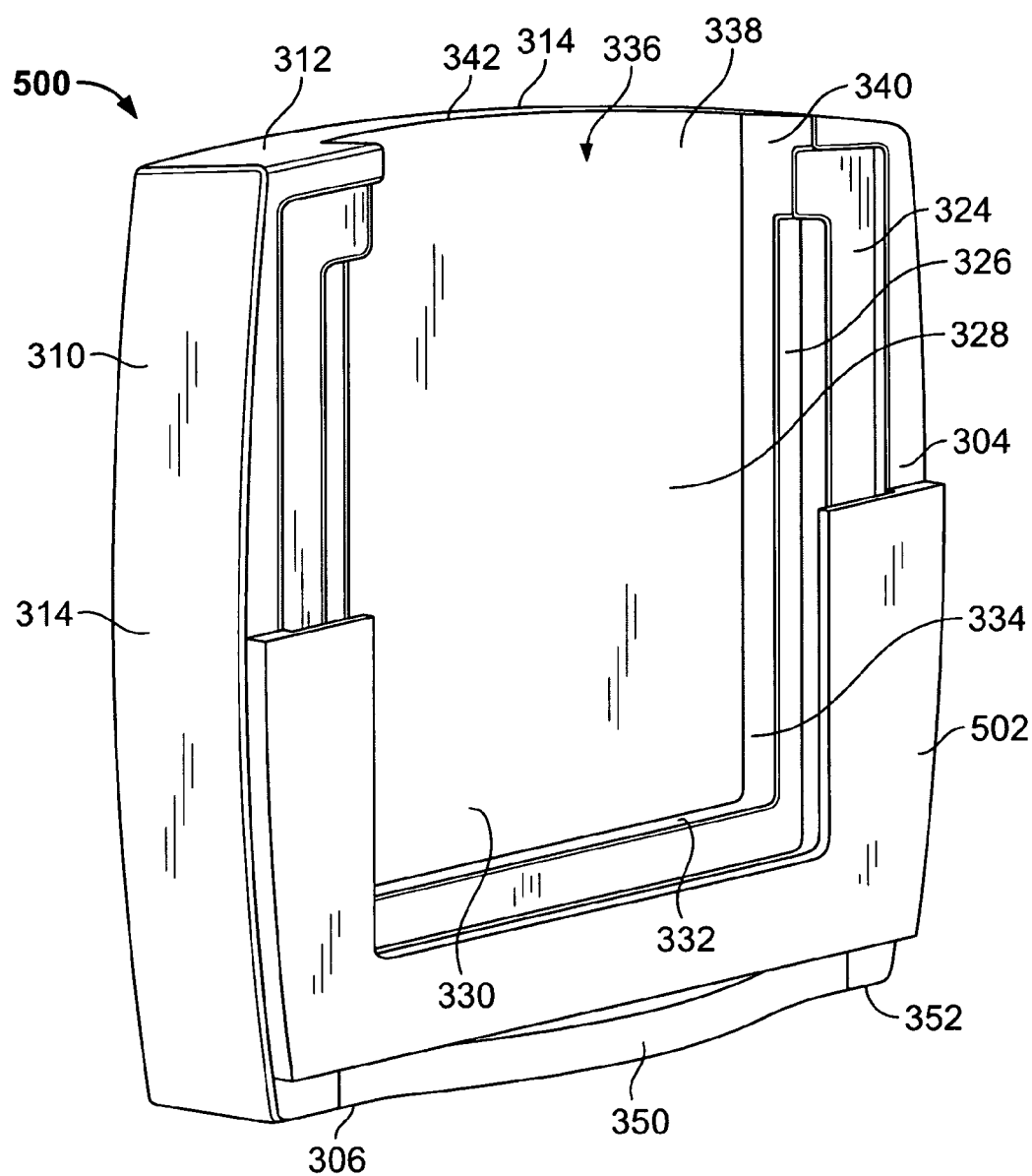
FIG. 40 is a rear isometric view of a tenth embodiment of the dispensing system, similar to the one depicted in FIG. 28 further including a dispenser and a refill holder.

Any of the embodiments disclosed herein may be accordingly modified in a manner known by those skilled in the art to include a channel that provides access to an inner recess adapted to hold a decorative element between walls defining the recess and a portion of a fragrance dispenser. For example, FIG. 38 depicts an eighth embodiment of a display frame 400 similar to the third embodiment depicted in FIGS. 15-17. However, a stepped recess 402, similar to the one depicted in FIGS. 26-32, is provided in the rear face 40 in lieu of the slot 80. The stepped recess includes an outer recess 404 and an inner recess 406 to provide a space for a dispenser and a decorative element (not shown). A channel 408 is also provided for receipt of the decorative element. While the frame 400 is similar to the previously depicted embodiments, the present embodiment is illustrative of the varying forms that stepped recesses and dispensers may comprise. A ninth embodiment of a display frame 450 is shown in FIG. 39, which is similar to the first embodiment depicted in FIGS. 1-7 and the fourth embodiment depicted in FIGS. 18-20 with the exclusion of the slot 80. A stepped recess that is identical to the stepped recess 322 depicted in FIGS. 26-32 is provided within the rear face 40 of the frame 450. A top end 452 of the frame 450 includes a wave-like shape. Further, any of the embodiments incorporated herein by reference may be similarly modified to include a channel that provides access to an inner recess adapted to hold a decorative element between walls defining the recess and a portion of a fragrance dispenser. For example, FIG. 40 depicts a tenth embodiment of a display frame 500 that includes a refill holder 502 identical to the one described in the Attorney Docket No. J-4297 patent application. The refill holder 502 may be modified in any manner as described in the J-4297 application and attached to the present display frame 500. The present embodiment affords the user the ability to releasably insert and remove the decorative element 14 and the dispenser 12 so that one or more of the decorative element 14 and the dispenser 12 may be replaced. Any of the display frames 400, 450, 500 may be similarly modified as the display frame 300. For example, the display frame 500 could include the protrusions 331 or upraised portions 348 to assist in retaining the decorative element 14 within the inner recess 328, particularly if the cup-shaped structure 26 and the peripheral flange 20 of the dispenser 12 are spaced wholly or partially from the medial recess 326 or peripheral recess 324, respectively.

It is intended that various modifications to the structure described herein be considered within the scope of the present disclosure. Further, it is intended that the disclosure presented in connection with the embodiments depicted in FIGS. 26-40 may be used to modify the embodiments described in connection with FIGS. 1-25 and vice versa. For example, the channel 336 may be disposed in the bottom, left, or right wall 306-310 of the display frame 300 as opposed to the top wall 312 or the protrusions 331 could be disposed within the deep central recess 54 of the display frame 10 described in connection with FIGS. 1-25.

INDUSTRIAL APPLICABILITY

The volatile material dispensing system described herein advantageously combines the functional and aesthetic characteristics of a picture frame with a fragrance dispenser. Thus, the use of one unit versus two individual units in a home or office setting may be enjoyed.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A picture display frame, comprising:
   a display frame having front and rear sides;
   an outer recess disposed within the rear side of the display frame;
   a volatile material holder disposed within the outer recess of the rear side, the volatile material holder including a reservoir and a vapor permeable membrane; and
   a slot disposed in a side wall of the display frame in communication with an inner recess defined by a bottom wall of the volatile material holder and a continuous bottom surface of the display frame, wherein the inner recess is adapted to hold a decorative element.

2. The picture display frame of claim 1, wherein the inner recess has at least one of a height and a width within a range of about 30 mm to about 60 mm.

3. The picture display frame of claim 1, wherein the inner recess has a thickness within a range of about 1 mm to about 5 mm.

4. The picture display frame of claim 1, wherein a protrusion extends outwardly from the rear side.

5. The picture display frame of claim 1, wherein the decorative element is an image comprising at least one of a photograph, a picture, and a drawing.

6. The picture display frame of claim 1, wherein the decorative element substantially obstructs a view of the reservoir through the front side of the picture display frame when disposed within the inner recess.

7. The picture display frame of claim 1, wherein the decorative element is centered within the display frame when disposed within the inner recess.

8. A display frame, comprising:
   a frame having front and rear faces;
   a stepped recess disposed within the rear face of the frame, wherein the stepped recess includes an outer recess, a medial recess, and an inner recess;
   a dispenser disposed within the outer and medial recesses, the dispenser including a vapor permeable membrane; and
   a channel disposed in a side wall of the display frame in communication with the stepped recess,
   wherein the inner recess is adapted to hold a decorative element.

9. The display frame of claim 8, wherein the dispenser includes a flange extending about a periphery of a blister, and wherein the flange is disposed within the outer recess and the blister is disposed within the medial recess.

10. The display frame of claim 9, wherein a bottom wall of the blister is spaced from a bottom surface of the inner recess.

11. The display frame of claim 10, wherein peripheral portions of the bottom wall are spaced from side walls of the medial recess.

12. The display frame of claim 11, wherein at least one protrusion is disposed on the side walls of the medial recess.

13. the display frame of claim 8 further comprising means for preventing at least one of lateral and longitudinal movement of the decorative element.

14. The display frame of claim 8, wherein the inner recess is substantially square and defined by a bottom surface, a bottom wall, two side walls, and an open top end.

15. The display frame of claim 14, wherein a first end of the decorative element rests upon the bottom wall of the inner recess.

16. A frame for displaying a decorative element, comprising:
   a frame having a dispenser disposed in a face thereof;
   a channel extending from an exterior surface of the frame to a void within an interior thereof, the void defined by a bottom wall of the dispenser directed toward the interior of the frame and recessed portions of the frame, which include a bottom surface; and
   at least one protrusion extending outwardly from the recessed portions of the frame disposed between the bottom wall of the dispenser and the bottom surface of the frame,
   wherein the channel is adapted to allow for the insertion of a decorative element into the void.

17. The frame of claim 16, wherein the frame is a uniform block and the dispenser is substantially flush with the face of the frame.

18. The frame of claim 16, further comprising a plurality of protrusions extending outwardly from the recessed portions of the frame disposed between the bottom wall of the dispenser and the bottom surface of the frame, wherein the plurality of protrusions are spaced generally symmetrically around a periphery of the void.

19. The frame of claim 18, wherein the plurality of protrusions form a wave-like pattern.

20. The frame of claim 16, wherein substantially all of the face of the frame is exposed to an ambient atmosphere.

* * * * *